United States Patent [19]

Venter et al.

[11] Patent Number: 5,474,898
[45] Date of Patent: Dec. 12, 1995

[54] OCTOPAMINE RECEPTOR

[75] Inventors: John C. Venter; Claire M. Fraser; William R. McCombie, all of Silver Spring, Md.

[73] Assignee: The United States of America as represented by the Department of Health and Human Services, Washington, D.C.

[21] Appl. No.: 194,338

[22] Filed: Feb. 8, 1994

Related U.S. Application Data

[62] Division of Ser. No. 676,174, Mar. 28, 1991, Pat. No. 5,344,776.

[51] Int. Cl.$^6$ .................................................. C07K 14/705
[52] U.S. Cl. ............................................. 435/6; 530/350
[58] Field of Search ................................. 435/6; 530/350

[56] References Cited

PUBLICATIONS

Neuron 2:343–354, Mar. 1990, Arakawa et al Cloning, Localization and Permanent Expression of a Drosophila Octopamine Receptor.

EMBO J. 9(11): 3611–3617, No. 1990, Sandou et al. Cloning and Characterization of a Drosophila Tyramine Receptor.

J. Biol Chem. 264 (2): 11754–11761 (15 Ju. 1984) Fraser et al. Cloning, Sequence Analysis and Permanent Expression of a Human–$\alpha_2$ Adrenergic Receptor in Chinese Hamster.

Axelrod, et al., "Octopamine", *Nature*, 265:501–504, 1977.

Battelle, et al., "Neurotransmitter Synthesis in *Limulus* Ventral Nerve Photoreceptors[1]", *Experientia*, 35/6:778–780, 1978.

Battelle, et al., "Targets of Octopamine Action in the Lobster: Cyclic Nucleotide Changes and Physiological Effects in Hemolymph Heart and Exoskeletal Muscle,", *The Journal of Pharmacology and Experimental Therapeutics* 205:2:438–448, 1978.

Blobel, et al., "Transfer of Proteins Across Membranes", *The Journal of Cell Biology*, 67:852–862, 1975.

Bodnaryk, "Identification of Specific Dopamine—and Octopamine–Senstive Adenylate Cyclases in the Brain of *Mamestra Configurata* WLK.", *Insect Biochem.*, 9:155–162, 1979.

Bunzow, et al., "Cloning and Expression of a Rat $D_2$ Dopamine Receptor cDNA", *Nature*, 336:783–787, 1988.

Casey, et al., "G Protein Involvement in Receptor–Effector Coupling", *The Journal of Biological Chemistry*, 263:6:2577–2580, 1988.

Chung, et al., "Cloning and Sequence Analysis of the Human Brain β–Adrenergic Receptor", *FEBS Lett.*, 211:2:200–206, 1987.

Chung, et al., "Site–Directed Mutagenesis and Continuous Expression of Human β–Adrenergic Receptors", *The Journal of Biological Chemistry*, 263:9:4052–4055, 1988.

Cotecchia, et al., "Molecular Cloning and Expression of the cDNA for the Hamster $\alpha_1$–Adrenergic Receptor", *Proc Natl. Acad. Sci. USA*, 85:7159–7163, 1988.

Dao, et al., "Effect of Cyproheptadine on the Octopamine–Induced Responses in the Mammalian Central Nervous System[1]", *Experientia*, 36:584–585, 1980.

Dixon, et al., "Cloning of the Gene and cDNA for Mammalian β–Adrenergic Receptor and Homology with Rhodopsin", *Nature*, 321:75–79, 1986.

Evans, "Multiple Receptor Types for Octopamine in the Locust", *J.Physiol.*, 318:99–122, 1981.

Evans, "Phenyliminoimidazolidine Derivatives Activate both Octopamine$_1$ and Octopamine$_2$ Receptor Subtypes in Locust Skeletal Muscle", *J. exp. Biol.*, 129:239–250, 1987.

Evans, et al., "Activities of Octopamine and Synephrine Stereoisomers on Octopaminergic Receptor Subtypes in Locust Skeletal Muscle", *J. Pharm. Pharmacol.*, 40:855–861, 1988.

Fraser, et al., "SITE–Directed Mutagenesis of Human β–Adrenergic Receptors: Substitution of Aspartic Acid–130 by Asparagine Produces a Receptor with High–Affinity Agonist Binding that is Uncoupled from Adenylate Cyclase", *Proc. Natl. Acad. Sci. USA*, 85:5478–5482, 1988.

Frielle, et al., "Cloning of the cDNA for the Human $\beta_1$–Adrenergic Receptor", *Proc. Natl. Acad. Sci. USA*, 84:7920–7924, 1987.

Gocayne, et al., "Primary Structure of Ray Cardiac β–Adrenergic and Muscarinic Cholinergic Receptors Obtained by Automated DNA Sequence Analysis: Further Evidence for a Multigene Family", *Proc. Natl. Acad. Sci. USA*, 84:8296–8300, 1987.

Harmar, et al., "Octopamine–Sensitive Adenylate Cyclase in Cockroach Brain: Effects of Agonists, Antagonists, and Guaynylyl Nucleotides", *Molecular Pharmacology*, 13:512–520, 1976.

Harris–Warrick, et al., "Cellular Mechanisms for Modulation of Posture by Octopamine and Serotonin in the Lobster[1]", *The Journal of Neuroscience*, 4:8:1976–1993, 1984.

Hicks, et al., "Actions of Octopamine Upon Dorsal Horn Neurones of the Spinal Cord", *Brain Research*, 157:402–406, 1978.

Hicks, et al., "Comparison of the Actions of Octopamine and Catecholamines on Single Neurones of the Rat Cerebral Cortex", *Br. J. Pharmac.*, 64:485–491, 1978.

Julis, et al., "Molecular Characterization of a Functional cDNA Encoding the Serotonin 1c Receptor", *Science*, 241:558–564, 1988.

(List continued on next page.)

*Primary Examiner*—Stephen G. Walsh
*Assistant Examiner*—John D. Ulm
*Attorney, Agent, or Firm*—Knobbe, Martens, Olson & Bear

[57] ABSTRACT

The present invention pertains in general to invertebrate octopamine receptor proteins and to polynucleotides encoding such receptors. The present invention also relates to insect for example, Drosophila octopamine receptors that are recombinantly expressed in mammalian cells where the receptor mediates the attenuation of adenylate cyclase activity and exhibits a pharmacological profile that is unique but closely related to mammalian adrenergic receptors. The present invention further relates to drug screening methods for the development of specific human pharmacological drugs and insecticides targeted for the octopamine receptor system.

5 Claims, 18 Drawing Sheets

OTHER PUBLICATIONS

Konishi, et al., "The Physiological Properties of Amine–Containing Neurones in the Lobster Nervous System", *J. Physiol.*, 279:215–229, 1978.

Kravitz, et al., "Amines and a Peptide as Neurohormones in Lobsters: Actions on Neuromuscular Preparations and Preliminary Behavioural Studies", *J. exp. Biol.*, 89:159–175, 1980.

Livingstone, et al., "Biochemistry and Ultrastructure of Serotonergic Nerve Endings in the Lobster: Serotonin and Octopamine are Contained in Different Nerve Endings", *Journal of Neurobiology*, 12:1:27–54, 1981.

Lochrie, et al., "G Protein Multiplicity in Eukaryotic Signal Transduction Systems", *Biochemistry*, 27:14:4957–4965, 1988.

Nathanson, et al., "Octopamine–Sensitive Adenylate Cyclase: Evidence for a Biiological Role of Octopamine in Nervous Tissue", *Science*, 180:308–310, 1973.

Nathanson, et al., "Octopamine Receptors, Adenosine 3',5'–Monophosphate, and Neural Control of Firefly Flasing", *Science*, 203:65–68, 1979.

Onai et al., "Cloning, Sequence Analysis and Chromosome Localization of a *Drosophila Muscarinic* Acetylcholine Receptor", *FEBS Lett.*, 255:2:219–255, 1989.

Regan, et al., "Cloning and Expression of a Human Kidney cDNA for an $\alpha_2$–Adrenergic Receptor Subtype", *Proc. Natl. Acad. Sci. USA*, 85:6301–6305, 1988.

Uzzan, et al., "Aminergic Receptors in *Drosophila Melanogaster*: Responsiveness of Adenylate Cyclase to Putative Neurotransmitters", *Journal of Neurochemistry*, 38:6:1542–1550, 1982.

Venter, et al., "Evolution of Neurotransmitter Receptor Systems", *Progess in Neurobiology*, 30:105–169, 1988.

Venter, et al., "Molecular Biology of Adrenergic and Muscarinic Cholinergic Receptors", *Biochemical Pharmacology*, 38:8:1197–1208, 1989.

Walker, et al., "The First Family (Adrenaline, Noradrenaline, Dopamine, Octopamine, Tyramine, Phenylethanolamine and Phenylethylamine)", *Comp. Biochem. Physiol.*, 61C:261–266, 1978.

Yarden et al., "The Avian $\beta$–Adrenergic Receptor: Primary Structure and Membrane Topology", *Proc. Natl. Acad. Sci. USA*, 83:6795–6799, 1986.

FIG. 1B

```
      AspAspAspAlaGlyMetGlyThrGluAlaValAlaAlaAsnIle
133   GATGACGATGCGGGCATGGGAACGGAGGCGGTGGCTAACATA                    222

SerGlySerLeuValGluGlyGluThrThrValThrAlaAlaLeuSer
223   TCCGGCTCGTGGTGGAGGGCCCTGACCACCGTTACCGCGGCATTGAGT              312

ThrAlaGlnAlaAspLysAspSerAlaGlyGluCysGluGlyAlaVal
313   ACGGCTCAGGCGGACAAGGACTCAGCGGGAGAATGCGAAGGAGCTGTG              402

GluLeuHisAlaSerIleLeuGlyLeuGlnLeuAlaVal
403   GAGGAGCTGCATGCCAGTATCCTGGGCCTCCAGCTGGCTGTG                    492

ProGluTrpGluAlaGluThrAlaGluValGluSerValIleIle
493   CCGGAGTGGGAGGCCGAAACCGCTGAGGTTGAGTCTGTCATTATC                 582

ValGluThrIleIleGlyAsnIleGlyValIleGluSerVal
      GTGCTGACCATCATCGGGAACATCCTGGTGATTCTGAGTGTG

PheThrTyrLysProLeuArgIleValGlnAsnPhePheIleValSer
      TTCACCTACAAGCCGCTGCGCATCGTCCAGAACTTCTTCATAGTTTCG

LeuAlaValAlaAspLeuThrValAlaLeuLeuValLeuPro
      CTGGCGGTGGCCGATCTCACGGTGGCCCTTCTGGTGCTGCCC

PheAsnValAlaTyrSerIleLeuGlyArgTrpGluPheGlyIleHis
      TTCAACGTCGCTTACTCGATCCTGGGCGCTGGGAGTTCGGCATCCAC

LeuCysLysLeuTrpLeuThrCysAspValLeuCysCysThr
      CTGTGCAAGCTGTGGCTCACCTGCGACGTGCTGTGCTGCACT
```

FIG. IC

```
583  SerSerIleLeuAsnLeuCysAlaIleAlaLeuAspArgTyrTrpAla
     AGCTCCATCCTGAACCTGTGTGCCATAGCCCTGACCGGTACTGGGC       672

673  IleThrAspProIleAsnTyrAlaGlnLysArgThrValGly
     CATTACGGACCCATCAACTATGCCCAGAGAGGACCGTTGGT            762

763  ArgValLeuLeuIleSerGlyValTrpLeuLeuSerLeuIle
     CGCGTCCTGCTCCATCTCCGGGGTGTGGCTACTTTCGCTGCTGATA       852

853  SerSerProProLeuIleGlyTrpAsnAspTrpProAspGlu
     AGTAGTCCGCCGTTGATCGGCTGGAACGACTGGCCGGACGAG          942

943  PheThrSerAlaThrProCysGluLeuThrSerGlnArgGlyTyrVal
     TTCACAAGCGCCACGCCCTGCGAGCTGACCTCGCAGGAGGCTACGTG     1032

IleTyrSerSerLeuGlySerPhePheIleProLeuAlaIle
     ATCTACTCCTCGCTGGGCTCCTTCTTTATCCCGCTGGCCATC

MetThrIleValTyrIleGluIleThrArgArgArgArgLeu
     ATGACGATCGTCTACATCGAGATCTTCGTGGCCACGCGGCGCCTA

ArgGluArgAlaArgAlaAsnLysLeuAsnThrIleAlaLeu
     AGGGAGCGAGCCAGGGCCAACAAGCTTAACACGATCGCTCTG

LysSerThrGluLeuGluProMetAlaAsnSerProValAlaAla
     AAGTCCACTGAGCTCGAGCCGATGGCAAACTCCTCCGCCGTCGCCGCC

SerAsnSerGlySerLysSerArgLeuLeuAlaSerTrpLeu
     TCCAACTCCGGCTCCAAGTCGCGTCTCCTAGCCAGCTGGCTT
```

FIG. 1D

```
      CysCysGlyArgAspArgAlaGlnPheAlaThrProMetIleGlnAsn
1033  TGCTGCGGCCGGGATCGGGCCAGTTCGCCACGCCTATGATCCAGAAC      1122

AspGlnGluSerIleSerSerGluThrHisGlnProGlnAsp
1123  GACCAGGAGAGCATCAGCAGTGAAACCCACCAGCCGCAGGAT            1212

SerSerLysAlaGlyProHisGlyAsnSerAspProGlnGlnHis
1213  TCCTCCAAAGCGGGTCCCCATGGCAACAGCGATCCCCAACAGCAGCAC      1302

ValValLeuValLysSerArgArgAlaLysThrLys
1303  GTGGTCCTGGTCAAGAGTCGCGTCGCCAAGACCAAG                  1392

AspSerIleLysHisGlyLysThrArgGlyGlyArgLysSerGlnSer
1393  GACTCCATTAAGCACGGCAAGACCCGTGGCCGCAAGTCGCAGTCC         1482

SerSerThrCysGluProHisGlyGluGlnLeuLeuPro
1483  TCGTCCACATGCGAGCCCCACGGCGAGCAACAGCTCTTACCC            1572

AlaGlyAspGlySerCysGlnProGlyGlyHisSerGly
      GCCGGCGGGGATGGCAGCTGCCAGCCCGGCGAGGCCACTCTGGA

GlyGlyLysSerAspAlaGluIleSerGluSerGlySer
      GGCGGAAAGTCGGACGCCGAGATCAGCGAGAGCGGGAGC

AspProLysGlyCysIleGlnValCysValThrGlyAlaAspGluGly
      GATCCCAAAGGTTGCATACAGGTCTGCGTGACTCAGGCGGACGAGCAA

ThrSerLeuLysThrProProGlySerSerThrGlyVal
      ACGTCCCTAAAGCTGACCCCGCCGCAATCCTCGACGGAGTC

AlaAlaValSerValThrProLeuGlnLysThrSerGlyValAsn
      GCTGCCGTTTCTGTCACTCCGTTGCAGAAGAAGACTAGTGGGTTAAC

GlnPheIleGluGluLysLysIleSerGluLysGlu
      CAGTTCATTGAGGAGAAACAGAAGATCTCGCTTTCCAAGGAG
```

FIG. 1E

```
     ArgArgAlaAlaArgThrLeuGlyIleLeuGluMetGlyValPheValGly
1573 CGGCGAGCGGCTCGCCACCCTGGGCATCATGGGCGTGTTCGTCATC        1662

CysTrpLeuProPhePheLeuMetTyrValIleLeuProPhe
1663 TGCTGGCTGCCCTTCTTCCTCATGTACGTCATTCTGCCCTTC           1752

CysGlnThrCysCysProThrAsnLysPheLysAsnPheIleThrTrp
1753 TGCCAGACCTGCTGCCCCACGAACAAGTTCAAGAACTTCATCACCTGG     1842

LeuGlyTyrIleAsnSerGlyLeuAsnProValIleTyrThr
1843 CTGGGCTACATCAACTCGGGCCTGAATCCGGTCATCTACACC           1932

IlePheAsnLeuAspTyrArgArgAlaPheLysArgLeuLeuGlyLeu
1933 ATCTTCAACCTGGACTACCGCCGGGCCTTCAAGCGACTTCTGGGCCTG     2022

Asn
2023 AATTGAGGCTGGCTGGCGGGGGTGGAAGATATAAACCG              2112

2113 GGCCAATCATGGTTCGAGCGGGAGAGCGTACCTCAAAGTTTGTGCCAA     2202
     ACTTAAATGGTCGTGTATGCGTTCAGCGGAGATCTCAGTCTA

TGTACAGTTGGACCCCCAGTTGATGAACTTCCGAGTTCAACTTCTCTA
     ACACATATATACTTTCAAATGCCCTTCTTGGTGAACTCATTTT

GAAGAAGTGGATGAATTTGGTAAAGTGTAATAGATGAATATAATTTT
     TAATGTTTAACGTTTCGGCAAAGTGAAAAGCCCCACATTGG

AAAGTCAAAGATGAGACTCGAGTGTATATATAGTTTCAAACTAAGTTA
     TTATTTCTAGCCGTAATTAAAATACTTTCATTTAGTTTTGAA
```

FIG. IF

```
2203  CATTTTTTAATATATTGTTGTTTGGAATCGATTGAGATGTACCACCA
      CATTAAGCGTAGATTGTTGTTCAATACTCATACTAAAATGGGTTG              2292

2293  TGCTGCGATTAAAGTGAGGATGTTGCCTCAAGGCACAGCTACTAGGAA
      AATCATAAAAATTACATGGTAAAGAATTATACATGCATTATA                  2382

2383  CTCCAGCTAAGTGGCATCCCAAACGAGAATAGCATCAAATTGAATTTA
      ATACAATTAAATTAAATGTTTAGGCACAAAGAATTGTGGCAA                  2472

2473  CTTTCGTGTTTCACCCTAAGCGTATGGATAACCAAAAAGTGTTTGTT
      AAATTAAAATCTGCGCTAAGATATGTAAGCAACTACTAAGCT                  2562

2563  AAATAATAACTTCCAAGAGAGAAACGTTTCTAGGCATTACTTTAACG
      ATTTGTATTTATATGTACTTAATTGTAGGTAAACGATAAAC                   2652

2653  CACTATACCTAATGTATACTTTCAAATACGCTTTGGACTATTGTTAA
      ATAATTAACGATTAATTGTTTTTATGCATAGCAACTATTG                    2742

2743  TGTTGAGTGGGCAGCTTAAAGCTAGCACATCGAAACTTACTTAAGGTA
      GATAAATGTTTAACTGCACGTTACGAAATGCAACAGAGTTGG                  2832

2833  CGAAAGGACGTAATTCAATGGATGTGTTAACTCAAGTACATGCTATAT
      CGRAAATGTATATCACAATTTATGTCTTTTAAGCACGACGATGTA               2922

2923  CGATAGTTTCACTAATTATATTGTTTAACGAGAAAGAGCGAGCAAAGC
      GTAAATGAAACAAATAAAAGACACATTCGAATTAAAGTTAGG                  3012

3013  AATTC                                                       3017
```

FIG. 3A

```
           1                                                          50
OCTDRS     ..........mp sadqilfvnv tttvaaaalt aaaavsttks gngnaargyt
A1HAM      .................................................
A2BHUM     ..........................maspala aalavaaaag pnasgagerg
B1HUM      ...........................................m gagvlvlgas
B1TUR      ..............................................mgdgwlppd
B2HAM      .................................................
B2RAT      .................................................
D2RAT      .................................................
M2RAT      .................................................
MDRS       mepvmslala ahgppsilep lfrtvttstt ttttttstt tttaspagys
S1CRAT     ..............................................mvn
                                      *
Consensus  ---------- ---------- ---------- ---------- ----------

51                                                        100
OCTDRS     dsdddagmgt eavanisgsl veglttvtaa lstagadkds agecegavee
A1HAM      .......... .mnpdldtgh ntsapaqwge lkdanftgpn qtssnstlpq
A2BHUM     sggvanasga swgppprgqys agav..................
B1HUM      epgnlssaap lpdgaataar llvpasppas llppase...............
B1TUR      cgphnrsggg gataaptgsr qv.....................
B2HAM      ..........................................mgppgn dsdflittng
B2RAT      ..........................................mephgn dsdfllapng
D2RAT      ..........................................mdplnls wydddlerqn
M2RAT      ..........................................mnnstn
MDRS       pgypgttllt alfenltsta asglydpysg myngtngti qfetkgprys
S1CRAT     lgnavrsllm hligllvwqf disispvaai vtdtfnssdg grlfq....
                *
Consensus  ---------- ---------- ---------- ---------- ----------
```

FIG. 3B

Transmembrane I

```
           101                                                          150
OCTDRS     lhasilglql avpeweallt alvlsviivl tiIGNiLvil SvftykpLri
A1HAM      ldvt...... .......... ralisv glvlgafilf alvGNILvll Svacnrhlrt
A2BHUM     .......... .......... ..agl aavvgflivf tVvGNVLVvi AvltsraLra
A2HUM      aratpyslqv .......titl vclagllmll tVfGNVLVll AvftsraLka
B1HUM      .......spe plsqqwtagm gllmalivll iVaGNVLviv Alaktpriqt
B1TUR      .......sae llsqqweagm sllmalvvll iVaGNVLvla Algrtqrlqt
B2HAM      shvpdhdvte erdeawvvgm ailmsvivla lVfGNVLvlt Alakferlqt
B2RAT      srapghditq erdeawvvgm ailmsvivla lVfGNVLvlt Alakferlqt
D2RAT      wsrpfngseg kadrphypyy amlltllifi iVfGNVLvcm Avsrekalqt
M2RAT      ssnnglaits pyktfevvfl vlvaggsislv tiiGNILvmv Sikvsrhlqt
MDRS       las....... .......mvvm gfvaailstv tVaGNVMVml SfkidkqLqt
S1CRAT     .......... .fpdgvqnwp alsivviiim tigGNILvim Avsmekklhn Consensus  ---------- ---------- ---------- --V-GNVLV-- -A------L-
```

Transmembrane II

```
           151                                                          200
OCTDRS     vgNffIvsLA vADltVAllv Lp.fnvaysl lgrWefGihl CklWlTcDvL
A1HAM      ptNyfIvnla iADllltSftv Lp.fsatIev lgyWvlGrif CdiWaAvDvL
A2BHUM     pqNlfLVsLA sADilVAtlv Mp.fslanel mayWyfGqvw CgvYlAlDvL
A2HUM      pqNlfLVsLA saDilVAtlv Ip.fslanev mgyWyfGktw CeiYLAlDvL
B1HUM      ltNlfImsLA sADivMGllv Vp.fgativv wgrWeyGsff CelWtSvDvL
B1TUR      ltNlfItsLA caDivMGllv Vp.fgativv wgrWeyGsfl CecWtSlDvL
B2HAM      vtNyfIsLA  cADlvMGlav Vp.fgashil rgtWlwGsfl CefWtSiDvL
B2RAT      vtNyfItsLa cADlvMGlav Vp.fgashil mkmWnfGnfw CefWtSiDvL
D2RAT      tNylIvsLa  vADllVAtlv Mp.wvvylev mkmWnfGnfw CefWtSiDvL
M2RAT      vnNyfLfsLA cADliIGvfs Mnlytlytv. vgeWkfSrih CdiFvTlDvM
MDRS       isNyfLfsLA iADfalGais Mplfavtti. igyWplGpvv CdIWlAlDyV
S1CRAT     atNyfLmsLA iADmlVGllv Mpllsllaily dyvWplPryl CdtWlAlDyL Consensus  --N--I--LA -AD--VG--- -M-------- ---W---G--- C--W---D-L
```

FIG. 3C

```
                    Transmembrane III                              Transmem-
          201                                                            250
OCTDRS    cctSSIInLc  aIAldDRYwaI  tdPinyaqkr  Tvgrvlllis  gvwLLsllis
A1HAM     cctASIlsLc  aISiDRYigv   ryslqyptlv  Trrkaila Ll svwvLstvis
A2BHUM    fctSSIvhLc  aISlDRYwsv   tgAveynlkr  Tprrvkatlv  avwIIsavis
A2HUM     fctSSIvhLc  aISlDRYwsI   tqAleynlkr  Tprrikailii tvwvIsavis
B1HUM     cvtASIetLc  vIAldDRYlaI  tsPfryqsll  Trararglvc  tvwaIsalvs
B1TUR     cvtASIetLc  vIAiDRYlaI   tsPfryqslm  Trarakviic  tvwaIsalvs
B2HAM     cvtASIetLc  vIAvDRYlaI   tsPfkvqsll  Traakarmvll mvwiVsqIts
B2RAT     cvtASIetLc  vIAvDRYiaI   tsPfkyqsll  Tknkarmvll  mvwiVsgits
D2RAT     mctASIlnLc  aISiDRYtaV   amPmlyntry  Sskrrvtvmi  alvwVlsfti
M2RAT     vsnASVmnLl  ilsfDRYfcV   tkPltypvkr  Ttkmagmmla  aawvLsfilw
MDRS      asnASVlnLl  ilsfDRYfsV   trPltyrakr  Ttnraavmlg  aawgIslllw
S1CRAT    fstASImhLc  aISlDRYvaI   rnPiehsrfn  Srtkalmkla  lvwaIsigvs Consensus ---ASI--L-  -IS-DRY--I   ---P------  T-------I-  ---I------ brane IV                                      Transmem-
          251
OCTDRS    sppligwndw  .pdeftsa..  ........tpc eltsQrgyvi ysslgSFFiP
A1HAM     igpllgwkep  apndd.....  ........kec gvteEpfyal fSslgSFYiP
A2BHUM    fpplvslyrq  ........    .pdgaaypqc  glndEtwyil  sSciqSFFaP
A2HUM     fpplisiekk  ggg.......  ggpqpaeprc  eindQkwyvi  aScigsFFaP
B1HUM     flpilmhwwr  a....esdea  rrcyndpkcc  dfvtNrayai  aSsvvSFYvP
B1TUR     flpimmhwwr  ....dedpqa  lkcyqdpgcc  dfvtNrayai  aSsiiSFYiP
B2HAM     fipiqmhwyr  athqkaidcy  ...hketcc   dffttNqayai aSsivSFYvP
B2RAT     flpiqmhwyr  athkqaidcy  a....ketcc  dfftNqayai  aSsivSFYvP
D2RAT     scplifqlnm  tdqne.....  ........    ciianpafvv  ySsivSFYvP
M2RAT     apallfwqfi  ........    ........vgv rtvedgecyi  qffsNaavtf gTaiaAFY1P
MDRS      ppwlyswpyi  ........    ........gkr tvpkdecyiq  fietNqyitf gTalaAFyfP
S1CRAT    vpipviglrd  e.........  ........    .skvfvnntt  cvlnDpnfvl iGsfVAFFiP Consensus ----------  ----------   ----N-----  ------S---  -SFY-P
```

FIG. 3D

```
                brane V
          301                                                       350
OCTDRS    laImtivYie   ifvatrrrlr   era.......   ..........   ..........
A1HAM     laVilvmYdr   vyivakrttk   nleag.....   ..........   ..........
A2BHUM    cIImglvYar   iyrvakrrtr   ..........   ..........   ..........
A2HUM     clImilvyyr   iyqiakrrtr   vpp.......   ..........   ..........
B1HUM     icImafvYlr   vfreaqkqvk   ..........   ..........   ..........
B1TUR     llImifvYlr   vyreakeqir   ..........   ..........   ..........
B2HAM     lvVmfvYsr    vfqvakr...   ..........   ..........   ..........
B2RAT     lvVmfvYsr    vfqvakr...   ..........   ..........   ..........
D2RAT     fiVtilvYik   iyivlrkrrk   ..........   ..........   ..........
M2RAT     vilmtvlywh   israsksrik   kekk......   ..........   ..........
MDRS      vtImcflYwr   iwretkkrqk   dlpnlqagkk   dsskrsnssd   entvvnhasg
S1CRAT    ltImvityFl   tiyvlrrqtl   mlrg......   ..........   ..........

Consensus ----I-----   --------Y-   ----------   ----------   ----------

351                                                       400
OCTDRS    ..........   ..........   ..........   ..........   ..........
A1HAM     ..........   ..........   ..........   ..........   ..........
A2BHUM    ..........   ..........   ..........   ..........   ..........
A2HUM     ..........   ..........   ..........   ..........   ..........
B1HUM     ..........   ..........   ..........   ..........   ..........
B1TUR     ..........   ..........   ..........   ..........   ..........
B2HAM     ..........   ..........   ..........   ..........   ..........
B2RAT     ..........   ..........   ..........   ..........   ..........
D2RAT     ..........   ..........   ..........   ..........   ..........
M2RAT     ..........   ..........   ..........   ..........   ..........
MDRS      gllafaqvgg   ndhdtwrrpr   sessadaesv   ymtnmvidsg   yhgmharkss
S1CRAT    ..........   ..........   ..........   ..........   ..........

Consensus ----------   ----------   ----------   ----------   ----------
```

FIG. 3E

```
        401                                                      450
OCTDRS  ..........  ..........  ..........  ..........  ..........
A1HAM   ..........  ..........  ..........  ..........  ..........
A2BHUM  ..........  ..........  ..........  ..........  ..........
A2HUM   ..........  ..........  ..........  ..........  ..........
B1HUM   ..........  ..........  ..........  ..........  ...kidsce
B1TUR   ..........  ..........  ..........  ..........  ...kidrce
B2HAM   ..........  ..........  ..........  ..........  ..........
B2RAT   ..........  ..........  ..........  ..........  ..........
D2RAT   ..........  ..........  ..........  ..........  ..........
M2RAT   ikstntikks  ytcfgsikew  ciawwhsgre  dsddfayege  epsdlgctsm
MDRS    ..........  ..........  ..........  ..........  ..........
S1CRAT  ..........  ..........  ..........  ..........  ..........

Consensus  ----------  ----------  ----------  ----------  ----------

*
        451                                                      500
OCTDRS  ..........  ..ranklnt   ialkstelep  mansspvaas  nsgsksrlla
A1HAM   ..........  ..vm kemsnskelt  lrihsknfhe dt........  ..........
A2BHUM  ..........  ..........  .........t  lsekrapvgp dg........
A2HUM   .srrgpdava  appggterrp  nglgpersag  pggaeaeplp
B1HUM   rrflggparp  pspspspvpa  papppgpprp  aa........  ..........
B1TUR   grfygsqeqp  qppp......  ..........  ..........  ..........
B2HAM   ..........  ..........  ql qkidksegrf  hs........  ..........
B2RAT   ..........  ..........  ql qkidksegrf  ha........  ..........
D2RAT   ..........  ..........  ......ep    vanqdpvsps lvqgr.....
M2RAT   ..........  ..........  ......ep    vanqdpvsps lvqgr.....
MDRS    ..........  ..........  illsdvsptp  lprpplasis  qlqemsavta
S1CRAT  nvmrdnysmg  gsvsavrpps  ..........  ..rv ntkrssrafr
        ...hteeel   anmslnflnc  cckknggeee  na........  ..........

Consensus  ----------  ----------  ----------  ----------  ----------
```

FIG. 3F

```
              501                                                      550
OCTDRS    swlccgrdra gfatpmiqnd qesissethq pqdsskagp. ..........
A1HAM     .......... .......... .......... .......... ..........
A2BHUM    .......... ..asptteng lgaaageart gtarprppt. ..........
A2HUM     tqlngapgep apagprdtda ldleeess.. .......... ..........
B1HUM     .......... .......... .......... .......... ..........
B1TUR     .......... .......... .......... .......... ..........
B2HAM     .......... .......... .......... .......... ..........
B2RAT     .......... .......... .......... .......... ..........
D2RAT     .anlktplkda arrageleme mlsstapper tryspipps. ..........
M2RAT     .......... ....ivkpn nnnmpg.... .......... ..........
MDRS      sttanvntag ngngainnnn nashngngav ngngagngag iglgttgnat
S1CRAT    .......... .......... .......... .......... ..........

Consensus ---------- ---------- ---------- ---------- ----------

551                                                      600
OCTDRS    .......... ..hqnsdpq qqhvvvlvkk srraktkdsi khqktrggrk
A1HAM     .......... .......... .......... .......... ..........
A2BHUM    .......... .......... .......... .......... .wartraaqr
A2HUM     .......... .......... .......... ..sd haerpppgprr
B1HUM     .......... .......... .......... .......... ..........
B1TUR     .......... .......... .......... .......... ..........
B2HAM     .......... .......... .......... .......... ..........
B2RAT     .......... .......... .......... .......... ..........
D2RAT     .......... .......... .......... .......... ..........
M2RAT     .......gdgg lehnkiqngk aprdgvtetc vqgeekessn
MDRS      hrdsrtlpvi nrinsrsvsq dsvytilirl psdgassnaa nggggpgag
S1CRAT    .......... .......... .......... .......... ..........

Consensus ---------- ---------- ---------- ---------- ----------
```

FIG. 3G

```
              601                                                           650
OCTDRS    sqssstceph ge.........  qqllpaggdg gscqpggghs gggksdaeis
A1HAM     .......... .......... .......... .......... ..........
A2BHUM    prgga..... .......... ...pgplrr ggrrragaeg gaggadgqga
A2HUM     pergprgkgk arasqvkpgd slrgagrgrr ggrrlqgrg rsasglprrr
B1HUM     .......... .......... .......... .......... ..........
B1TUR     .......... .......... .......... .......... ..........
B2RAT     .......... .......... .......... .......... ..........
D2RAT     .......... .......... ........h hqltlpdpsh hglhsnpdsp
M2RAT     dstssaavas nnrddeitqd entvstsldh srddnskqtc ikivtkaqkg
MDRS      aaasaslsmq gdcapsikmi hedqpttaa aa..plasaa atrrplpsrd
S1CRAT    .......... .......... .......... .......... ..........

Consensus ---------- ---------- ---------- ---------- ----------

651                                                           700
OCTDRS    tesgadpkgc iqvcvt..qa deqtslkltp pqsstgvaav svtplqkkts
A1HAM     .......... .......... .......... .......... ..lsstkakg
A2BHUM    gpgaaqsga. .......... ltasrspppg grlsrassrs vefflsrrrr
A2HUM     agaqgq.... .......... .......... .......... ..........
B1HUM     .......... .......... .......... .......... .lpqhqpilg
B1TUR     .......... .......... .......... .......... .pnlgqveqd
B2RAT     .......... .......... .......... .......... .qnlsqveqd
D2RAT     akpeknghak ivnpriakff eiqt...mpn gktrtslktm s.........
M2RAT     dvytptsttv elv....... .......... ..gssgqsqd elqnvvarki
MDRS      sefslplgrr mshaqhdarl lnakvipkql qkagggaagg gvggahalmn
S1CRAT    .......... .......... .......... .......p npnpdqkprr Consensus ---------- ---------- ---------- ---------- ----------
```

FIG. 3H

```
                                                                    Transmembrane VI
                    701                                                                    750
OCTDRS    qvnqfieekq  kislskErRa  artlgilmgv  FvlcWlPFfl  myvilpfc.q
A1HAM     hnprssiavk  lfkfsrEkKa  aktlgivvgm  FilcWlPFfi  alplgslfst
A2BHUM    a..rssvcrr  kvaqarEkRf  tfvlavVmgv  FvLcWfPFff  iyslygicr.
A2HUM     ....        ..nrEkRf    tfvLavVigv  FvVcWfPFff  tytltavgc.
B1HUM     ngragkrrps  rlvaleEqKa  lktlgilmgv  FtLcWlPFfl  anvvkafh..
B1TUR     ngraskrkts  rvmamrEhKa  lktLqiImgv  FtLcWlPFfi  vnlvnvfn..
B2HAM     grsghglrrs  skfclkEhKa  lktLqiImgt  FtLcWlPFfi  vnivhviq..
B2RAT     grsghglrss  skfclkEhKa  lktLgiImgt  FtLcWlPFfi  vnivhvir..
D2RAT     ..      rr  klsqqkEkKa  tqmLaiVlgv  FilcWlPFfi  thilnlhc..
M2RAT     vkmpkqpakk  kpppsrEkKv  trtIlaFlla  FiItWaPYnv  mvlintfc..
MDRS      arnaakkkkk  sqekrqEsKa  aktLsaIlls  FiItWtPYni  lvlikplt..
S1CRAT    kkkekrprgt  mqainnEkKa  skvLgiVffv  FlImWcPFfi  tnilsvlc..

Consensus ----------  ------E-K-  ----L--I--- F-L-W-PF--  ----------

Transmembrane VII
                    751                                                                    800
OCTDRS    tccp......  ..........  ..thkfknfi  twlgYInSgl  NPviYtifnl
A1HAM     lkp.......  ..........  ..pdavfkvv  twlgYfnScl  NPilYpcgsk
A2BHUM    ..........  .......eac  qvpgplfkff  fwigYcnSsI  NPvlYtvfnq
A2HUM     ..........  ..........  svprtlfkff  fwfgYcnSsl  NPviYtifnh
B1HUM     ..........  .........re lvpdrlfvff  nwlgYanSaf  NPilY.crsp
B1TUR     ..........  .........rd lvpdwlfvff  nwlgYanSaf  NPliy.crsp
B2HAM     ..........  .........dn lipkevyill  nwlgYvnSaf  NPLiY.crsp
B2RAT     ..........  .........an lipkevyill  nwlgYvnSaf  NPIiY.crsp
D2RAT     ..........  .........dc nippvlysaf  twlgYvnSav  NPIiYttfni
M2RAT     ..........  .........ap cipntvwtig  ywlcYInStI  NPacYalcna
MDRS      ..........  ......tcsd  ciptelwdff  yalcYInstI  NPmcYalcna
S1CRAT    ..........  .....gkacnq klmekllnvf  vwigYvcSgi  NPivYtlfnk Consensus ----------  ----------  ----------  ---Y--S---  NP--Y-----
```

FIG. 3I

```
            801                                                            850
OCTDRS      dYRrAFkrlL gln....... .......... .......... ..........
A1HAM       eFKrAFmriL gcqcrsgrrr rrrrrlgaca ytyrpwtrgg slersqsrkd
A2BHUM      dFRaSFkhiL frrrrgfrq. .......... .......... ..........
A2HUM       dFRrAFkkiL crgdrkriv. .......... .......... ..........
B1HUM       dFRkAFgclL ccarraarrr hathgdrpra sgclarpcpp pspcaasddd
B1TUR       dFRkAFkrlL cfprkadrrl haggqpaplp ggfistlgsp ehspggtwsd
B2HAM       dFRiAFgelL clrrssskay gngyssnsng ktdymgeasg cqlgqekese
B2RAT       dFRiAFgelL clrrssskty gngyssnsng rtdytgeqsa yqlgqekene
D2RAT       eFRkAFmkiL hc........ r......... .......... ..........
M2RAT       tFKkTFkhlL schyknigat .......... .......... ..........
MDRS        tFRrTYvriL tckwhtrnre gmvrqvyn.. .......... ..........
S1CRAT      iYRrAFskyL rcdykpdkkp pvrqiprva. .......... ..........

Consensus   -FR-AF---L ---------- ---------- ---------- ----------

851                                                            900
OCTDRS      .......... .......... .......... .......... ..........
A1HAM       slddsgscms gsqrtlpsas pspgylgrga qpplelcayp ewksgallsl
A2BHUM      .......... .......... .......... .......... ..........
A2HUM       .......... .......... .......... .......... ..........
B1HUM       dddvvcatpp arllepwa.. .......... gcngcaaads dssldepcrp
B1TUR       cnggtrggse ssleerhskt srseskmere knilattrfy ctflgngdka
B2HAM       rlc....... edppgtesfv ncqgtvpsls ldsggrncst ndspl.....
B2RAT       llc....... eeapgmegfv ncqgtvpsls idsggrncnt ndspl.....
D2RAT       .......... .......... .......... .......... ..........
M2RAT       .......... .......... .......... .......... ..........
MDRS        ..atalsgre invniyrhtn ervarkandp epgiemqven lelpvnpsnv
S1CRAT      .......... .......... .......... .......... ..........

Consensus   ---------- ---------- ---------- ---------- ----------
```

FIG. 3J

```
              901                                                      950
OCTDRS        ..........  ..........  ..........  ..........  ..........
A1HAM         peppgrrgrl  dsgplftfkl  lgepespgte  gdasnggcda  ttdlangqpg
A2BHUM        ..........  ..........  ..........  ..........  ..........
A2HUM         ..........  ..........  ..........  ..........  ..........
B1HUM         gfasesk...  ..........  ..........  ..........  ..........
B1TUR         vfctvlrivk  lfedatctcp  hthlklmkwr  fkqhga....  ..........
B2HAM         ..........  ..........  ..........  ..........  ..........
B2RAT         ..........  ..........  ..........  ..........  ..........
D2RAT         ..........  ..........  ..........  ..........  ..........
M2RAT         ..........  ..........  ..........  ..........  ..........
MDRS          ..........  ..........  ..........  ..........  ..........
S1CRAT        vserissv..  ..........  ..........  ..........  ..........

Consensus     ----------  ----------  ----------  ----------  ----------

951        962
OCTDRS        ..........  ..
A1HAM         fksnmplapg  hf
A2BHUM        ..........  ..
A2HUM         ..........  ..
B1HUM         ..........  ..
B1TUR         ..........  ..
B2HAM         ..........  ..
B2RAT         ..........  ..
D2RAT         ..........  ..
M2RAT         ..........  ..
MDRS          ..........  ..
S1CRAT        ..........  ..

Consensus     ----------  --
```

5,474,898

OCTOPAMINE RECEPTOR

This is a divisional of application Ser. No. 07/676,174 filed on Mar. 28, 1991 now U.S. Pat. No. 5,344,776.

FIELD OF THE INVENTION

The present invention pertains, in general, to invertebrate octopamine receptor proteins and to polynucleotides encoding such receptors. The present invention relates in particular, to invertebrate receptors that are recombinantly expressed in mammalian cells. The receptor proteins of the invention mediate the attenuation of adenylate cyclase activity and exhibit a pharmacological profile that is unique but closely related to mammalian adrenergic receptors.

The present invention further relates to drug screening methods for the development of specific human pharmacological drugs and insecticides targeted for the octopamine receptor system.

BACKGROUND INFORMATION

Octopamine, a biogenic amine, plays a major role as a transmitter, hormone, and neuromodulator in invertebrates (see P. D. Evans, *Adv. Insect Physiol.* 15:317–473 (1980), for review). Through the use of pharmacological and biochemical assays, specific receptors for octopamine have been identified in many invertebrate phyla, including arthropods and molluscs (J. A. Nathanson and P. Greengard, *Science*. 180:308–310 (1973); J. Axelrod and J. M. Saavedra, *Nature* 265:501–504 (1977); A. J. Harmer and A. S. Horn, *Mol. Pharmacol.* 13:512–520 (1977); R. J. Walker and G. A. Kerkut, *Comp. Biochem.* 61C:261–266 (1978); S. Konishi and E. A. Kravits, *J. Physiol.* 279:215–229 (1978); B. Battelle and E. A. Kravits, *J. Pharmacol. Exp. Ther.* 205:438–448 (1978); J. A. Nathanson, Science. 203: 65–68 (1979); R. P. Bodnaryk, *Insect Biochem.* 9: 155–162 (1979); B. Battelle et al., *Experientia* 35:778 (1979); E. A. Kravits et al., *J. Expo Biol.* 89:159–175 (1980); P. D. Evans, *J. Physiol.* 318:99–122 (1981) and P. D. Evans, *J. Exp. Bio.* 129:239–250 (1987); M. S. Livingston et al., *J. Neurobiol.* 12: 27–54 (1981); A. Uzzan and Y. Dudai, *J. Neurochem.* 38:1542–1550 (1982); R. M. Harris-Warrick and E. A. Kravitz, *J. Neurosci.* 4: 1976–1993 (1984); P. D. Evans et al., *J. Pharm. Pharmacol.* 40:855–861 (1988)). Pharmacological studies in insects have provided evidence for the existence of multiple subtypes of octopamine receptors (P. D. Evans, *Insect. Physiol.* 15:317–473 (1980), P. D. Evans, *J. Physiol.* 318:99–122 (1981), P. D. Evans, *J. Exp. Biol.* 129:239–250 (1987); P. D. Evans et al., *J. Pharm. Pharmacol.* 40:855–861 (1988)). In addition, there are reports indicating that octopamine receptors, pharmacologically distinct from adrenergic and dopamine receptors, exist in the mammalian central nervous system (T. P. Hicks and H. McLennan, *Brain Res.* 157:402–406 (1978), T. P. Hicks and H. McLennan, *Br. J. Pharmacol.* 64:485–491 (1978b); W. P. C. Dao and R. J. Walker, *Experientia* 36: 584–585 (1980))

Since octopamine receptors are selectively blocked by α-adrenergic antagonists and activated by α-adrenergic agonists, there has been speculation that octopamine receptors are closely related to vertebrate adrenergic receptors (P. D. Evans, *Adv. Insect Physiol.* 15:317–473 (1980), P. D. Evans, *J. Physiol.* 318:99–122 (1981), P. D. Evans, *J. Exp. Biol.* 129:239–250 (1987); J. C. Venter et al., *Biochem. Pharmacol.* 38:1197–1208 (1988)). However, there have been no structural data available to evaluate this hypothesis. Studies of octopamine receptors have also been complicated by the lack of specificity of available ligands both among the octopamine receptor subtypes and between octopamine receptors and receptors for other biogenic amines.

The present inventions are products, processes and compositions that relate, at least in part, to an octopamine receptor cDNA and to the protein product encoded therein. Sequence analysis of the cDNA reveals that the octopamine receptor is a member of the adrenergic/muscarinic/opsin gene superfamily of receptors (J. C. Venter et al., *Prog. Neurobiol.* 30:105–169 (1988; J. C. Venter et al., *Biochem. Pharmacol.* 38:1197–1208 (1989)). Permanent expression of this cDNA in mammalian cells provides the opportunity to study an octopamine receptor in isolation and thus, allows for the unambiguous description of a single receptor type. It also allows for a rapid and effective assay for the rational design in testing of insecticides targeted against the receptor.

SUMMARY OF THE INVENTION

It is an object of the present invention to provide a segment of a DNA molecule which codes for an octopamine receptor protein derived from invertebrates, for example, Drosophila, and the encoded proteins. It is another object of the present invention to provide a recombinant DNA molecule comprising a vector and a DNA segment which codes for the invertebrate octopamine receptor.

It is a further object of the present invention to provide a host cell stably transformed with the recombinant DNA molecule provided by this invention in a manner allowing expression of the octopamine receptor protein.

It is another object of the present invention to provide methods for screening potential pharmaceuticals and insecticides that are reactive to octopamine receptors and other related biogenic amine receptors. Such methods include a radiolabel binding and competition displacement assay and a metabolic assay that measures agonists and antagonists of octopamine mediated attenuation of adenylate cyclase.

Various other objects and advantages of the present invention will become obvious from the drawings and the detail description of the invention.

In one embodiment, the present invention relates to a DNA segment encoding all, or a unique portion, of an invertebrate octopamine receptor. An example of an invertebrate may be the insect, Drosophila.

In another embodiment, the present invention relates to a substantially pure form of Drosophila octopamine receptor.

In a further embodiment, the present invention relates to a recombinantly produced protein having all, or a unique portion, of the amino acid sequence FIGS. 3A-3J given in SEQ ID NO: 2.

In a further embodiment, the present invention relates to a recombinant DNA molecule comprising a DNA segment encoding all, or a unique portion, of an invertebrate octopamine receptor and a vector.

In yet a further embodiment, the present invention relates to a host cell stably transformed with the above recombinant DNA molecule in a manner allowing expression of invertebrate octopamine receptor protein encoded in the recombinant DNA molecule.

In another embodiment, the present invention relates to drug screening methods for detecting agonists and antagonists of octopamine receptors comprising the steps of contacting CHO-K1 cells that have been stably transformed and express recombinant octopamine receptor with the labeled ligand yohimbine in the presence or the absence of a specific agonist or antagonist, and measuring the amount of bound labeled ligand.

In yet another embodiment, the present invention relates to a method of screening drugs and insecticides that recognize biogenic amine receptors comprising the steps of incubating forskolin and a potential drug or insecticide in non-transfected and octopamine receptor transfected CHO-K1 cells and comparing the change in cAMP concentrations to control cells that have been incubated with forskolin alone.

The entire contents of all publications mentioned herein are hereby incorporated by reference.

BRIEF DESCRIPTION OF THE DRAWINGS

FIGS. 1A–1F shows the restriction map, sequencing strategy, and nucleotide (SEQ ID NO: 1) and deduced amino acid sequence (SEQ ID NO: 2) of the Drosophila octopamine receptor cDNA clone.

The nucleotide sequence is numbered from the first ATG of the coding region. Selected restriction sites are shown above the diagram. In the sequencing strategy diagram at the top of the figure, each arrow represents an individual clone that was sequenced at least once. The sequence has been submitted to GenBank and assigned the accession number M26181.

Figure 2A:
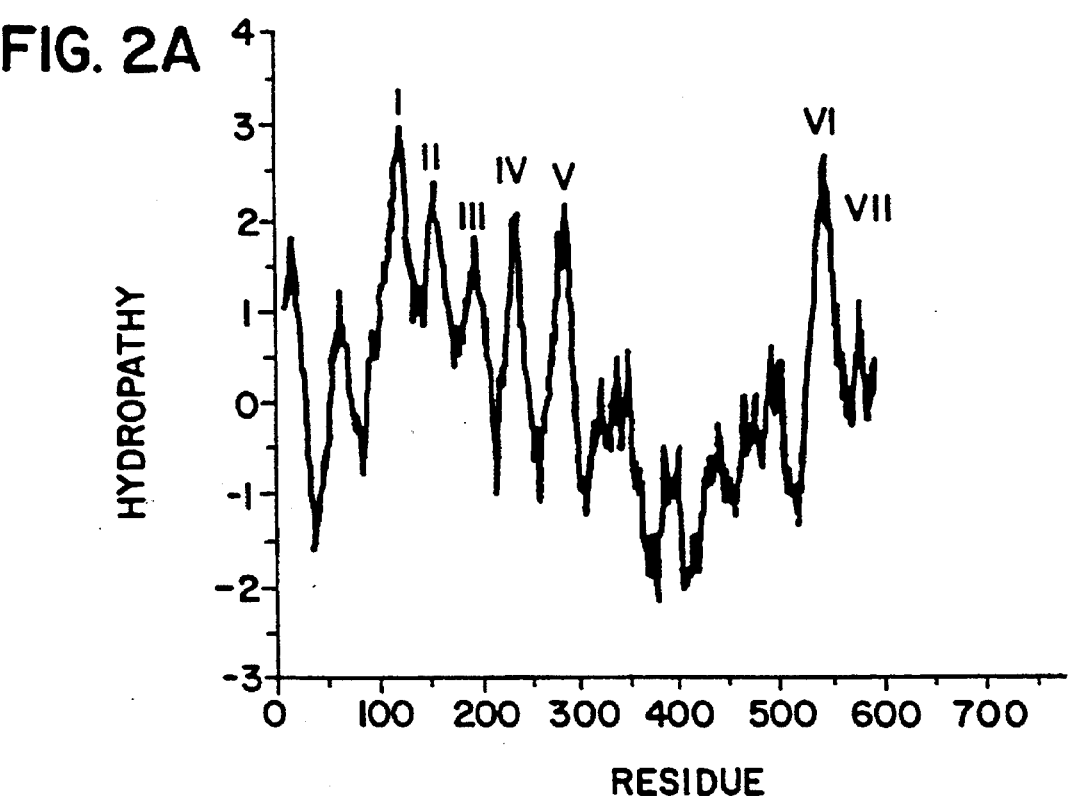
Figure 2B:
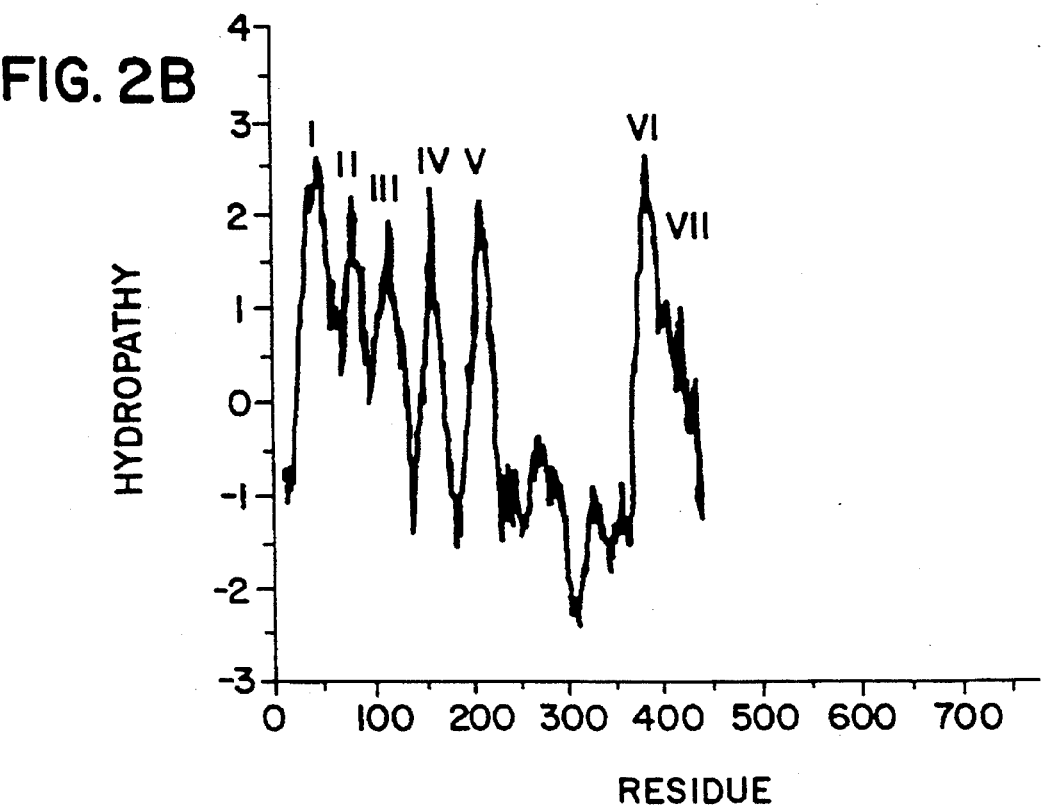

FIGS. 2A and 2B shows hydropathy analysis of Drosophila octopamine, receptor and the human $\alpha_2$-adrenergic receptor, respectively.

Hydropathy plots of Kyte and Doolittle (1982) were calculated using a window of 20 residues for both the Drosophila octopamine receptor and the human $\alpha_2$-adrenergic receptor (C. M. Fraser, *J.Biol. Chem.* 264:11754–11761 (1989a)). The predicted secondary structure of both receptors contained seven stretches of hydrophobic amino acids of sufficient length to span the bilayer, similar to the secondary structure of other members of the adrenergic/muscarinic/opsin gene superfamily. The Drosophila receptor also contains additional hydrophobic residues at its amino terminus that may play a role as a putative signal sequence, a feature observed in many membrane proteins (G. Blobel and B. Dobberstein, *J. Cell Biol.* 67:852–862 (1975); T. Onai et al., *FEBS Lett.* 255:219–225 (1989)).

FIGS. 3A–3J shows a comparison of the deduced amino acid sequences of the Drosophila octopamine, receptor with other members of the gene superfamily.

Amino acid sequences were aligned using the GAP Program of the University of Wisconsin Genetics Computer Group (J. Devereux et al., *Nucl. Acids Res.* 12:387–395 (1984)), with gaps introduced to maximize homology followed by minor manual alignments. Conserved amino acid residues, as defined by Dayhoff et al. (1978), were considered to be identical. The amino acid sequences shown represent those of the Drosophila octopamine, receptor (Octdrs; SEQ ID NO: 2), hamster $\alpha_1$-adrenergic receptor; SEQ ID NO: 3 (A1ham), human $\alpha_2$B and $\alpha_2$A-adrenergic receptors (A2b1hum and A2hum; SEQ ID NOS: 4 and 5, respectively), human and turkey $\beta_1$-adrenergic receptors (B1hum and B1tur; SEQ ID NOS: 6 and 7, respectively), hamster and rat $\beta_2$-adrenergic receptors (B2hum and B2rat; SEQ ID NOS: 8 and 9, respectively), rat D2 dopamine receptor (D2rat; SEQ ID NO: 10), rat and Drosophila muscarinic receptors (M2rat and Mdrs; SEQ ID NOS: 11 and 12), and rat 5HT1c receptor (S1crat; SEQ ID NO: 13). Homology is indicated in the consensus line (SEQ ID NO: 14) below the receptor sequences. Putative transmembrane regions are labeled. Conserved sites for N-linked glycosylation are indicated by an asterisk. Data are from the present study and from other works (R. Dixon et al., *Nature* 321:75–79 (1986); Y. Yarden et al., *Proc. Natl. Acad. Sci. USA* (1986); F. Z. Chung et al., *FEBS Lett.* 211:200–206 (1987); T. Frielle et al., *Proc. Natl. Acad. Sci. USA* 84:7920–7924 (1987); J. Gocayne et al., *Proc. Natl. Acad. Sci. USA* 84:8296–8300 (1987); S. Cotecchia et al., *Proc. Natl. Acad. Sci. USA* 85:7159–7163 (1988); J. W. Regan et al., *Proc. Natl. Acad. Sci. USA* 85:6301–6305 (1988); D. Julius et al., *Science* 241:558–563 (1988); T. Onai et al., *FEBS Lett.* 255:219–225 (1989); C. M. Fraser et al., *J. Biol. Chem.* 264:11754–11761 (1989a); J. R. Bunzow et al., *Nature* 336:783–787 (1988)).

Figure 4:
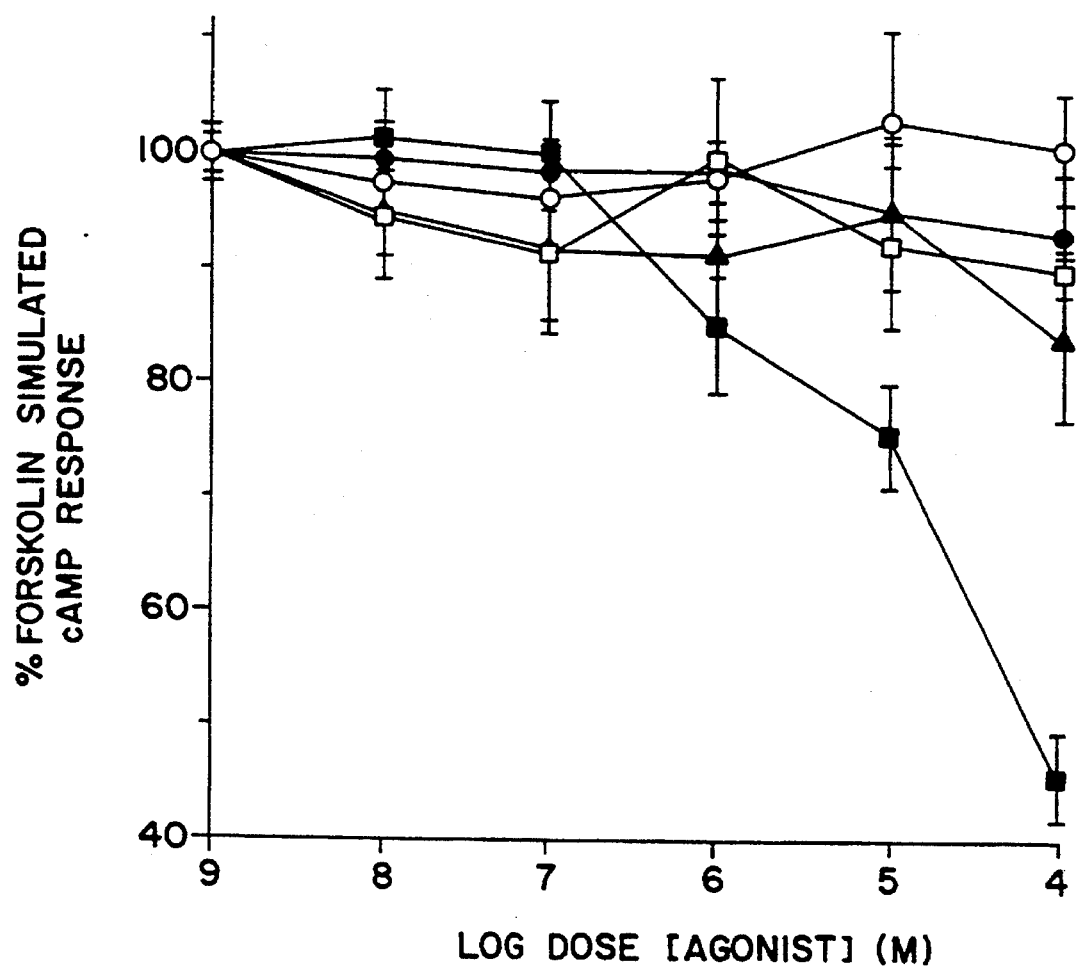

FIG. 4 shows the effect of biogenic amines on cAMP concentrations CHO-K1 cells expressing the Drosophila octopamine$_1$ receptor.

Transfected cells ($3\times10^5$ cells per dish) were washed once with PBS and incubated in PBS containing 1 mM 3-isobutyl-1-methylxanthine (Sigma) at 37° C. for 20 min. Agonists, at the indicated final concentrations, were added to the cultures along with 10 µM forskolin (Sigma), and cultures were incubated at 37° C. for an additional 20 min. Incubations were terminated by the addition of 6% trichloroacetic acid. Trichloroacetic acid extracts were extracted four times with distilled water-saturated ether, and cMAP concentrations were determined using a cAMP radioimmunoassay kit (New England Nuclear). Data are expressed as percent forskolin-stimulated cAMP production. In the indicated experiments, cell cultures were incubated with Bordetella pertussis islet activating protein (200 ng/ml; list biological lab) at 37° C. for 18 hr in normal culture medium prior to the assay of cAMP. Solid and open squares represent data obtained with octopamine in transfected and control cells, respectively. Solid circles represent data with epinephrine in transfected cells. Open triangles and open circles represent data with octopamine in transfected cells in the presence of 10 µM yohimbine or in cells pretreated with pertussis toxin, respectively. Data represent the average ±SEM of at least three separate experiments performed in duplicate.

DETAILED DESCRIPTION OF THE INVENTION

The present invention relates to segments of DNA which encode an octopamine receptor for invertebrates. In particular, the present invention relates to a DNA segment that encodes the octopamine receptor for the invertebrate, Drosophila. The DNA sequence analysis shown in FIG. 1A–1F and amino acid sequence analysis shown in FIG. 3A–3J demonstrate that the octopamine receptor is a member of the adrenergic/muscarinic/opsin gene superfamily of receptors.

The invention also relates to the invertebrate octopamine receptor proteins, for example, Drosophila octopamine receptors encoded by octopamine receptor DNA segments.

The octopamine protein found in invertebrates such as Drosophila has a calculated molecular weight, as determined by DNA sequence analysis of about 64,700 daltons. In another embodiment, the octopamine receptor has the amino acid sequence as set forth in FIGS. 3A–3J. The amino acid sequence of the Drosophila protein receptor displays significant homology with mammalian $\alpha$ and $\beta$ adrenergic receptors, rat and Drosophila muscarinic acetylcholine receptor and rat $D_2$ dopamine and 5HT receptors.

In another embodiment, the octopamine protein encoded by the Drosophila octopamine receptor gene is glycosylated, displaying conserved sites for N-linked glycosylation within the amino terminal domains similar to α- and β-adrenergic receptors described above. The octopamine receptor protein of the present invention is substantially free of proteins with which it is normally associated and can be bound to a solid support such as, for example, agarose, sepharose, plastic, nylon membrane or nitrocellulose paper.

The present invention also relates to a recombinant DNA molecule comprising a vector and the above-described DNA segment which encodes the invertebrate Drosophila octopamine receptor or unique portion thereof. Possible vectors include plasmids, for example, pSVL expression vector, and other vectors known in the art that either transiently or stably transform host cells in a manner which allows expression of the octopamine receptor proteins. Examples of appropriate eukaryotic cells include, for example, Chinese hamster kidney cells. Other eukaryotic cells such as Baculovirus and Schneider cells or prokaryotic expression systems could be adapted for the production of Drosophila octopamine proteins.

The present invention further relates to drug screening methods that may be useful in developing specific insecticides and human pharmaceutical drugs targeted against the octopamine receptor system. In a binding assay provided herein, octopamine receptor genes isolated from a specific DNA library are inserted into a plasmid expression vector and used to transfect a Chinese hamster kidney cell called CHO-K1 cells. These cells stably integrate the foreign DNA into the genome. Cells that express the insect octopamine receptor and process receptor into the mammalian cell membrane are cloned, expanded and frozen down for further use as membrane preparations in a ligand binding assay. In the assay disclosed herein, the membrane bound octopamine receptor preparations are incubated with labeled yohimbine, an α2-adrenergic receptor antagonist. Suitable labels include for example, radiolabels such as $^3H$. Transfected CHO-K1 cell membranes displace saturable, high affinity binding of labeled ligand yohimbine, with a calculated equilibrium dissociation constant described herein. No specific labeled ligand is observed bound to membranes prepared from control, untransfected CHO-K1 cells. The binding of potential drug agonists and antagonists to the insect octopamine receptor are examined in competition displacement studies with labeled yohimbine. Thus, in one method taught by the present invention, the membrane preparations are incubated with a fixed concentration of labeled yohimbine in the presence of increasing concentrations of either agonist or antagonist. After the incubations are terminated, the reaction mixture containing labeled ligand bound to receptor membranes is calculated by measuring label. Analogs of octopamine (agonists) display a stronger affinity for the octopamine receptor and displace labeled ligand whereas antagonists show a lower affinity for octopamine receptors and do not displace bound labeled ligand.

Another aspect of the present invention relates to another drug screening method that identifies new compounds with biogenic amine (agonists) or antagonist activity for biogenic receptors by measuring adenylate cyclase concentrations in transfected CHO-K1 cells expressing octopamine receptors. In one embodiment, potential drugs are tested for their ability to attenuate forskolin-stimulated adenylate cyclase activity. Forskolin is added to control or octopamine receptor transfected CHO-K1 cells that stimulates increased intracellular cAMP levels in transfected cells over basal CHO-K1 levels. In the presence of forskolin, known concentrations of octopamine are added and the attenuation of forskolin stimulated cyclase AMP is calculated. A potential antagonist is determined by the competitive reversal of octopamine mediated attenuation of forskolin stimulated cyclic AMP accumulation when the drug is added to the assayed transfected cells. A potential agonist drug will have no effect of forskolin stimulated cyclic AMP level in either transfected or control CHO-K1 cells.

The present invention further relates to methods of isolating other neurogenic and biogenic receptors using the octopamine receptor DNA segment described in the present invention. One skilled in the art will appreciate that the invention includes methods for isolating related octopamine receptors in other biogenic amine receptors using human genomic DNA libraries and a DNA segment encoding the octopamine receptor or a unique portion thereof as a probe in known cloning and nucleotide sequencing methods. One skilled in the art will also appreciate that such related receptors could be used in the methods described above for the design of screening of insesticides and drugs.

Certain aspects of the invention are described in greater detail in the non-limiting Examples that follow.

EXAMPLES

The following materials and procedures are referred to in the Examples that follow.

Screening of a Drosophila Genomic Library

Using a human brain $β_2$-adrenergic receptor as a hybridization probe, a Drosophila genomic library was screened under low stringency conditions (hybridization with 30% formamide, 6× SSC, 5× Denhardt's, 50 mM $NaPO_4$ [pH 7.4], 50 µg/ml sheared salmon sperm DNA for 18 hr at 49° C.; wash with 6× SSC, 0.1% SDS for 20 min at room temperature followed by 3× SSC for 20 min at room temperature). Three λgt11 clones were isolated, and a 367 bp BglII fragment of one of these clones was used to screen a cDNA library.

Screening of a Drosophila cDNA Library

The Drosophila head cDNA library was made from poly(A)$^+$ mRNA isolated from the heads of the Oregon-R strain of *D. melanogaster*. A 367 bp BglII fragment of the Drosophila genomic clone (DGSA1641; see C. M. Fraser et al., *J. Biol. Chem.* 264:11754–11761 (1989)) was radiolabeled by random priming for screening of the Drosophila cDNA library. The library was transferred to Hybond-N filters (Amersham) and screened with the $^{32}$P-labeled probe under the following hybridization conditions; 30% formamide, 6× SSC, 5× Denhardt's 50 mM sodium phosphate (pH 7.4), 50 µg/ml sheared salmon sperm DNA at 42° C. for 18 hr. Filters were washed in 2× SSC, 0.1% SDS and then in 0.5× SSC at 55° C. for 30 min each. Seven positive clones were isolated from the 6000,000 pfu screened; 6 of these displayed identical restriction maps.

Sequence Analysis of Drosophila cDNA Clones

A 3.3 kb EcoRI cDNA insert from 1 of the 6 identical clones that hybridized on Southern blots with the DGSA1641 probe at high stringency (0.5× SSC at 55° C. for 30 min) was isolated. Blunt ends were created with Klenow fragment of DNA polymerase, and the insert was subcloned in both orientations into the HincII site in the multiple cloning region of pVZ1 (A. Henikoff and M. K. Eghtedarzadeh, *Genetics* 17:711–725 (1987)). Exonuclease III digestion was performed at 37° C., and aliquots were removed every 30 s as described by Henikoff (1987). Single-stranded DNA was purified and prepared for sequence analysis using an Applied Biosystems 370A Automated DNA Sequencer (J.

Gocayne et al., *Proc. Natl. Acad. Sci. USA* 4:8296–8300 (1987)).

Expression of the Drosophila Receptor in CHO-K1 Cells

Based on analysis of open reading frames, the region of approximately 2.2 kb, as shown in FIGS. 1A–1F, was selected for expression in CHO-K1 cells. A 2.2 kb fragment as excised from pVZ1 by sequential enzyme cuts. The vector was linearized with ClaI, and blunt ends were generated with DNA polymerase. The cDNA fragment was released from the vector by cleavage with AlwNI. The AlwNI site is contained within the defined open reading frame and this necessitated reconstruction of the 5' end of the gene with a synthetic oligonucleotide. This was accomplished by ligating the gene fragment and the following synthetic oligonucleotide:

5'-CTAGATGCCATCGGCAGATCAAATCAAATC-3' (SEQ ID NO: 15)

3'-TACGGTAGCCGTCTAGTT-5' (SEQ ID NO: 16)

into pSVL that had been cleaved with XbaI and SmaI. The synthetic oligonucleotide reconstructs the 5' end of the gene, destroys the AlwNI site with a silent mutation, and adds a terminal XbaI site, which facilitates insertion of the fragment into the expression vector in a directional manner. The 5' portion of the fragment reconstructed for expression was excised from pSVL and ligated into M13 to confirm the sequence of the 5' end of the construct used for expression. pSVL containing the Drosophila receptor gene was cotransfected with pMSVneo, which contains the selective marker for G418 resistance, into CHO-K1 cells (American Type Culture Collection) using the calcium phosphate precipitation technique (C. M. Fraser et al., *Proc. Natl. Acad. Sci. USA* C. M. Fraser et al., *J. Biol. Chem.* 264:11754–11761 (1989) , C. M. Fraser et al., *Proc. Natl. Acad. Sci. USA* 85:5478–5482 (1989)). Stable transfectants were obtained by growth of the cells in culture medium containing the antibiotic, Geneticin (G418, 500 µg/ml; GIBCO). Colonies derived from single cells were isolated and expanded as described (C. M. Fraser et al., *Proc. Natl. Acad. Sci. USA* 85:5478–5482 (1988) , C. M. Fraser et al., *J. Biol Chem.* 264:11754–11761 (1989), C. M. Fraser et al., *Proc. Natl. Acad. Sci. USA* 85:5478–5482 (1989)) and those transfectants expressing the Drosophila gene were identified by Northern blot analysis of total cellular RNA.

Northern Analysis of Transfected CHO-K1 Cells Expressing the Drosophila Octopamine Receptor RNA was isolated from five 150 mm plates of confluent cells using guanidinium thiocyanate according to the method of Chirgwin et al., (1979). Total RNA (20 µg) from each line of transfected cells was separated on agarose gels containing formaldehyde as described by Maniatis et al. (1982). RNA was transferred to Hybond-N membranes (Amersham) in 25 mM NaPO4 buffer (pH 6.5), and the membrane was hybridized with the 3.3 kb Drosophila cDNA clone radiolabeled with [$^{32}$P]cytosine ($0.5 \times 10^6$ cpm/ml). The Northern blot was washed with 6× SSC, 0.1% SDS for 15 min at 42° C. 2× SSC for 20 rain at 42° C., 2× SSC for 30 min at 56° C., and 0.5× SSC for 30 min at 56° C.

Cell Membrane Preparation and Radioligand Binding Assays

Cell membranes from transfected cells were prepared as previously described (F.-Z. Chung et al., *J. Bol. Chem.* 263:4052–4055 (1988); C. M. Fraser et al., *Proc. Natl. Acad. Sci. USA* 85:5478–5482 (1988), C. M. Fraser et al., *J. Biol. Chem.* 264:11754–11761 (1989), C. M. Fraser et al., *Proc. Nat;. Acad. Sci. USA* 85:5478–5482 (1989)). [$^3$H]Yohimbine binding assays and competition displacement experiments were performed as described for the human $\alpha_2$-adrenergic receptor (C. M. Fraser et al., *J. Biol. Chem.* 264:11754–11761 (1989). Ligand binding data were analyzed using the LIGAND program of Munson and Rodbard (1980).

Example 1.

Octopamine Receptor Gene Cloning

The known nucleotide sequence similarities among G protein-linked receptors was exploited to search for genes related to adrenergic receptors in a Drosophila genomic library using a human brain $\beta_2$-adrenergic receptor cDNA clone (F.-Z. Chung et al., *FEBS Let.* 211:200–206 (1987)) as a hybridization probe. Using low stringency hybridization conditions, three λgt11 clones were isolated. Partial sequence analysis revealed that the genomic clones contained exons that, when translated, displayed high homology to the transmembrane domains of mammalian adrenergic receptor proteins. Using a 367 bp fragment of Drosophila genomic DNA (clone DGSA1641) that displayed homology with the putative sixth and seventh transmembrane domains of adrenergic receptors as a hybridization probe, a 3.3 kb cDNA clone from a Drosophila head cDNA library was isolated. This same 367 bp fragment of Drosophila genomic DNA was also used to isolate an $\alpha_2$-adrenergic receptor gene from a human genomic library (C. M. Fraser et al., *J. Biol. Chem.* 264:11754–11761 (1989)).

Example 2.

Sequencing Strategy and Protein Structure

Figure 1A:
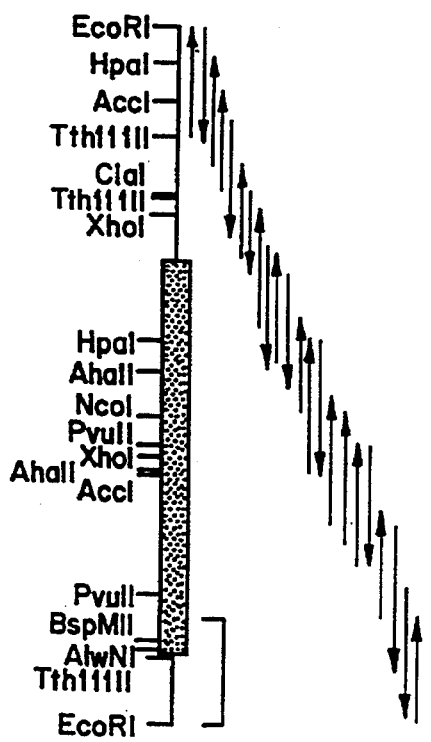

The sequencing strategy and restriction map of the 3.3 kb Drosophila cDNA clone are shown in FIG. 1A. This strategy was based upon the generation of overlapping, unidirectional exonuclease III deletions (S. Henikoff, *Meth. Enzymol.* 155:156–165 (1987)). Automated DNA sequence analysis was carried out using an Applied Biosystems 370A DNA Sequencer (J. Gocayne et al., *Proc. Natl. Acad. Sci. USA* 84:8296–8300 (1987)). As illustrated in FIG. 1, the nucleotide sequence of this clone contains 3335 bp and has a large open reading frame that encodes a protein of 601 amino acids with a calculated molecular mass of 64,700 daltons. This cDNA clone and genomic clone DGSA1641 (originally used as a hybridization probe) contained identical sequences.

Several features of this protein suggested that it belongs to the adrenergic/muscarinic/opsin, gene superfamily. Hydropathy profiles revealed seven stretches of hydrophobic amino acids of sufficient length to span the bilayer, similar to the secondary structure of other members of the gene superfamily (FIG. 2). However, unlike other members of this gene family, the Drosophila protein contains an additional sequence of hydrophobic residues at its amino terminus. The properties of this amino-terminal hydrophobic sequence suggest that it may function as a putative signal sequence, a feature observed in many membrane proteins (G. Blobel and B. Dobberstein, *J. Cell. Biol.* 67:852–862 (1975)). A similar region is also seen in the putative muscarinic acetylcholine receptor from Drosophila (T. Onai et al., *FEBS Lett.* 255:219–225 (1989)). As shown in FIGS. 3A–3J, the deduced amino acid sequence of the Drosophila protein displays significant homology with those of mammalian $\alpha$- and $\beta$-adrenergic receptors, rat and Drosophila muscarinic acetyl-choline receptors, and rat dopamine and 5 HT receptors (R. Dixon et al., *Nature* 321:75–79 (1986); Y. Yarden et al., *Proc. Natl. Acad. Sci. USA* 83:6795–6799

(1986); F.-Z. Chung et al., FEBS Lett. 211:200–206 (1987); T. Frielle et al., Proc. Natl. Acad. Sci. USA 84:7920–7924 (1987); J. Gocayne et al., Proc. Natl. Acad. Sci. USA 84:8296–8300 (1987); S. Cotecchia et al., Proc. Natl. Acad. Sci. USA 85:7159–7163 (1988); J. W. Regan et al., Proc. Natl. Acad. Sci. USA 85:6301–6305 (1988); D. Julius et al., J. Physiol. 318:99–122 (1988); T. Onai et al., FEBS Lett. 255:219–225 (1989); C. M. Fraser et al., J. Biol. Chem. 264:11754–11761 (1989a); J. R. Bunzow et al., Nature 336:783–787 (1988)). The Drosophila receptor exhibited highest homology with $\alpha_2$-adrenergic receptors (32% and 35% identity, increasing to 66% and 70% similarity with conserved substitutions for $\alpha_2 A$ and $\alpha_2 B$ receptors, respectively). The regions of greatest amino acid identity among these receptors reside within the putative transmembrane helices. All of these receptors display conserved sites for N-linked glycosylation within their amino-terminal domains and conserved aspartic acid residues in the second and third transmembrane helices; these have been shown by site-directed mutagenesis to be involved in agonist-induced receptor activation in β-adrenergic (F.-Z. Chung et al., J. Biol. Chem. 263:4052–4055 (1988); C. M. Fraser et al., Proc. Natl. Acad. Sci. USA 85:5478–5482 (1988)) and muscarinic acetylcholine (C. M. Fraser et al., J. Biol. Chem. 264:11754–11761 (1989)) receptors.

Example 3

Permanent Expression of the Drosophila cDNA Clone in Mammalian Cells

To prove the identity and characterize the Drosophila receptor further, 2.2 kb cDNA fragment containing the open reading frame was ligated into the expression vector pSVL and cotransfected with C. M. Fraser et al., Proc. Natl. Acad. Sci. USA 85:5478–5482 pMSVneo into CHO-K1 cells as previously described (F.-Z. Chung et al., J. Biol. Chem. 263:4052–4055 (1988); (1988)). Clonal cell lines that grew in selective medium containing Geneticin were isolated and expanded. Cell lines expressing the Drosophila cDNA fragment were identified by Northern blot analysis of total cellular RNA using the $^{32}$P-labeled Drosophila cDNA clone as a hybridization probe. Several clonal cell lines were identified that contained detectable levels of receptor-specific mRNA and one was chosen with the highest level for detailed pharmacological and biochemical studies.

Due to the sequence homology between the Drosophila cDNA clone and genes encoding mammalian $\alpha_2$-adrenergic receptors (C. M. Fraser et al., J. Biol. Chem. 264:11754–11761 (1989)), the assay was performed with [$^3$H]yohimbine, an $\alpha_2$-adrenergic receptor antagonist. Transfected CHO-K2 cell membranes displayed saturable, high-affinity binding of the radio-ligand [$^3$H]yohimbine, with a calculated equilibrium dissociation constant ($K_d$) of 6.2 nM and a $B_{max}$ of 1.75 pmol of receptor per mg of membrane protein (Table 1). No specific radioligand binding was observed to membranes prepared from control, untransfected CHO-K1 cells. The affinity of yohimbine for the octopamine receptor is similar to that for the human $\alpha_2$-adrenergic receptor expressed in CHO-K1 cells (3.5 nM; C. M. Fraser et al., J. Biol. Chem. 264:11754–11761 (1989)). The binding of a series of agonists and antagonists to the Drosophila receptor was examined in competition displacement studies with [$^3$H]yohimbine (Table 1). Synephrine, the N-methylated analog of octopamine, showed the highest agonist affinity ($K_i$=10.8±2.5 μM) for the Drosophila receptor, followed by the α-adrenergic agonist clonidine ($K_i$=21±7 μM), octopamine ($K_i$=29±6 μM), serotonin ($K_i$=75±18 μM), and epinephrine ($K_i$=139±41 μM). The β-adrenergic agonist isoproterenol and dopamine displayed low affinities for the Drosophila receptor ($K_i$s>1000 μM). Antagonists displayed a random order of potency for inhibition of [$^3$H]yohimbine binding of chlorpromazine ($K_i$=0.18+0.006 μM)>mianserin ($K_i$=1.2±0.3 μM)>phentolamine ($K_i$=2.2±0.7 μM)>cyproheptadine ($K_i$=2.6±0.5 μM)>metoclopramide ($K_i$=4.6±1.4 μM)>propranolol ($K_i$=5.3±1.6 μM). The rank orders of potency for agonist and antagonist displacement of [$^3$H]yohimbine binding to the Drosophila receptor strongly suggested that an octopamine receptor had been cloned (Evans, Insect. Physiol. 15:317–473 (1980), P. D. Evans, J. Physiol. 318:99–122 (1981), P. D. Evans, J. Exp. Biol. 129:239–250 (1987); P. D. Evans et al., J. Pharm. Pharmacol. 40:855–861 (1988)). The significantly greater receptor affinity for yohimbine and chlorpromazine as compared with metoclopramide suggested that this was an octopamine type 1 receptor subtype (see table 1; see also Evans, Insect. Physiol. 15:317–473 (1980), P. D. Evans, J. Physiol. 318:99–122 (1981), P. D. Evans, J. Exp. Biol. 129:239–250 (1987); P. D. Evans et al., J. Pharm. Pharmacol. 40:855–861 (1988)).

TABLE 1

Comparison of Affinites of Various Octopamine Receptors for Agonists and Antagonists

| | $K_1$ (μM)[a] | EC$_{50}$ (M) | | |
| --- | --- | --- | --- | --- |
| | | Octampamine$_1$[b] | Octapamine$_2$[b] | Octopamine$_{20}$[b] |
| Agonists | | | | |
| Synephrine(±) | 10.8 ± 2.5 | | | |
| Clonidine | 21 ± 7 | 6.8 × 10$^{-10c}$ | 6.4 × 10$^{-6c}$ | 2.0 × 10$^{5c}$ |
| Octopamine(±) | 29 ± 6 | | | |
| Serotonin | 75 ± 18 | | | |
| Epinephrine(−) | 139 ± 41 | | | |
| Dopamine | >1000 | | | |
| Isoproterenol(−) | >1000 | | | |
| Antagonists | | | | |
| Yohimbine[d] | 0.0062 ± 0.0004 | 2.8 × 10$^{-7c}$ | | |
| Chlorpromazine | 0.18 ± 0.06 | 2.6 × 10$^{-8c}$ | 1.6 × 10$^{4c}$ | 7.0 × 10$^{5c}$ |
| Mianserin | 1.2 ± 0.3 | 4.5 × 10$^{-6c}$ | 1.2 × 10$^{-6c,e}$ | 2.0 × 10$^{-5c,e}$ |
| Phentolamine | 2.2 ± 0.7 | 1.9 × 10$^{-9c}$ | | |

TABLE 1-continued

Comparison of Affinites of Various Octopamine Receptors for Agonists and Antagonists

|  | $K_1$ (μM)[a] | $EC_{50}$ (M) | | |
|---|---|---|---|---|
|  |  | Octampamine$_1$[b] | Octapamine$_2$[b] | Octopamine$_{20}$[b] |
| Cyproheptadine | 2.6 ± 0.5 | $3.7 \times 10^{-6c}$ | $2.2 \times 10^{-6c,e}$ | $5.1 \times 10^{-5c,e}$ |
| Metoclopramide | 4.6 ± 1.4 | No effect-$10^{-6e}$ | $1.0 \times 10^{-6c,e}$ | $9.5 \times 10^{-6c,e}$ |
| Propranolol(−) | 5.3 ± 1.6 | $5.4 \times 10^{-7e}$ | $2.9 \times 10^{-4e}$ | $4.0 \times 10^{-4e}$ |

Affinites of the Drosophilia octopamine receptor for agonists and antagonists. Membrane bound octopamine receptors (20 μg of protein) were incubated with 6 nM[$^3$H]yohimbine in the presence of increasing concentrations of the indicated agonists (0.1 μM to 2 mM) or antagonists (10 nM to 200 μM). Incubations were performed at 37° C. for 20 min in a final volume of 250 μl and terminated by filtration over Whatman GF/C glass fiber filters. Experiments were repeated three times in triplicate, and the average inhibition constants (± SD) were caluclated using the LIGAND program of Munson and Rodbard (1980).
[a]This work.
[b]This represents work done on a locust neuromuscular preparation.
[c]Data from Evans (1982).
[d]Values calculated from analysis of [$^1$H]yohimbine saturation binding isotherms (Munson and Rodbard, 1980).
[3]Data from Evans (1981).

Example 4

Octopamine-Mediated Attenuation of Adenylate Cyclase Activity

Numerous reports have described an octopamine-sensitive adenylate cyclase system in insects (J. A. Nathanson and P. Greengard, *Science.* 180:308–310 (1973); J. Axelrod and J. M. Saavedra, *Nature* 265:501–504 (1977); A. J. Harmer and A. S. Horn, *Mol. Pharmacol.* 13:512–520 (1977); B. Battlee and E. A. Kravits, *J. Pharmacol. Exp. Ther.* 205:438–448 (1978); J. A. Nathanson, *Science.* 203:65–68 (1979); R. P. Bodnaryk, *Insect Biochem.* 9:155–162 (1979); A. Uzzan and Y. Dudai, *J. Neurochem* 38:1542–1550 (1982); P. D. Evans, *J. Exp. Biol.* 129:239–250 (1987)); however, none of the agonists listed in Table 1 produced an increase over basal levels of intracellular cAMP in transfected CHO-K1 cells. These agonists also had no effect on phosphoinositide hydrolysis in transfected cells. Because of the pharmacological and structural similarities of the Drosophila receptor to mammalian $\alpha_a$-adrenergic receptors, the ability of octopamine to attenuate forskolin-stimulated adenylate cyclase activity was tested. Addition of forskolin (10 μM) to control or transfected CHO-K1 cells produced an average 35-fold increase in intracellular cAMP levels over basal values. As shown in FIG. 4, octopamine produced a dose-dependent attenuation of forskolin-stimulated cAMP levels in transfected cells that was not observed in control cells. In the presence of forskolin plus 100 μM octopamine, cAMP levels were only 46% of those seen with forskolin alone. Octopamine-mediated attenuation of forskolin stimulated cAMP accumulation was competitively antagonized by yohimbine (FIG. 4), whereas epinephrine had no effect on forskolin-stimulated cAMP levels in either transfected or control CHO-K1 cells (FIG. 4). Furthermore, in transfected cells pretreated with Bordetella pertussis islet activating protein, the ability of octopamine to attenuate forskolin-stimulated cAMP levels was abolished, suggesting that this response was mediated through a pertussis toxin-sensitive G protein (P. J. Casey and A. G. Gilman, *J. Biol. Chem.* 263:2577–2580 (1988); M. A. Lochrie and M. I. Simon, *Biochemistry* 27:4957–4965 (1988)), as is observed with the $\alpha_2$-adrenergic receptor (C. A. Fraser et al., *J. Biol. Chem.* 264:11754–11761 (1989)).

Example 5

Drosophila Chromosome and Tissue Localization

To determine where the octopamine receptor gene maps in the Drosophila genome, one of the genomic clones, DGSA1641, was biotinylated using a nick translation kit (Bethesda Research Laboratories) and biotin-11-dUTP (Enzo biochemical) and hybridized to Drosophila salivary gland polytene chromosomes. The clone was detected using a DNA detection kit (Bethesda Research Laboratories) following the procedures of Engel et al. (1985). The probe hybridized to a single site on the right arm of chromosome 3 at 99A10-B1. Studies are in progress to determine whether any of the known mutations that map to this site represent the octopamine receptor gene.

A Drosophila genomic Southern blot was probed with the octopamine receptor cDNA clone. Eight micrograms of genomic DNA isolated from the Canton-S wild-type strain (T. Jowett, Preparation of nucleic acids. In Drosophila: A practical Approach, D. B. Roberts, ed. (Washington, D.C.: IRL Press), pp. 275–277 (1986)) was digested with EcoRI, BamHI or HindIII and electrophoresed on a 0.6% agarose gel. Following capillary blotting, the filter was hybridized with the octopamine cDNA clone that had been $^{32}$P-labeled by the random primer method. The blot was hybridized overnight at 45° C. in 5× SSC, 0.05M sodium phosphate buffer (pH 6.8), 0.1% SDS, 5× Denhardt's, and 0.2 mg/ml denatured salmon sperm DNA. The blot was washed one time in 2× SSC, 0.1% SDS fir 30 min at room temperature followed by two 30 min washes at successive temperatures (45° C., 50° C., and 65° C.). The pattern of hybridization was the same regardless of wash temperature used in the 45° C.–65° C. range. There do not appear to be BamHI or EcoRI sites within this gene, since only single bands of 23 kb (BamHI) or 6.6 kb (EcoRI) appear in these lanes. The hybridization pattern was unchanged by washing at 45° C., 50° C., 55° C., or 65° C. Thus, under conditions used in this example DNA probe appears to be hybridizing to a single gene. This is consistent with other in situ hybridization studies, which also showed a single hybridization site. This gene does not appear to be highly polymorphic in the Canton-S wild-type strain. It remains to be determined whether lower stringency hybridization conditions can be used to isolate other pharmacologically distinct octopamine receptor genes.

Octopamine receptors have been found in the central and peripheral nervous systems of insects (P. D. Evans, *Adv. Insect Pysiol.* 15:317–473 (1980)) as well as in skeletal muscle (P. D. Evans, *J. Physiol.* 318:99–122 (1981), P. D. Evans, *J. Exp. Biol.* 129:239–250 (1987); P. D. Evans et al., *J. Pharm. Pharmacol.* 40:855–861 (1988)). To determine whether the cloned octopamine receptor gene showed differential expression in nervous system versus skeletal muscle and gut, a comparison was made between the intensity of hybridization of $^{32}$P-labeled cDNA to equivalent amounts of poly(A)$^+$ mRNA from Drosophila heads versus bodies. The heads are enriched in nervous system, whereas the bodies are enriched for skeletal muscle (from the flight muscles in the thorax) and for gut (in the abdomen). RNA was prepared from 1 g of heads and 2 g of bodies using the guanidinium isothiocyanate homogenization-CsCl centrifugation procedure (J. M. Chirgwin et al., *Biochemistry* 18:5294–5299 (1979)). Each preparation was enriched for poly(A)$^+$ mRNA by passing it through one Pharmacia oligo (dT) column according to the manufacturer's instructions. Approximately 8–9 μg of mRNA was added to each lane of a formaldehyde, 0.8% agarose gel. The electroblotted filter was prehybridized for 2 hr at 42° C. with 5× SSPE, 10× Denhardt's, 50% deionized formamide, 5 mg/ml denatured salmon sperm DNA and then hybridized overnight at 42° C. in 5× SSPE, 1× Denhardt's, 50% formamide, 1 mg/ml denatured salmon sperm DNA, 0.1% SDS using the cDNA probe labeled with $^{32}$P by the random primer method. The blot was washed as follows; a brief rinse in 2× SSC, 15 min in 2× SSC at room temperature, 15 min in 0.1× SSC at room temperature, and two 30 min washes in 0.1× SSC at 60° C. All washes contained 0.1% SDS. Heads are substantially enriched for a single 3.6 kb mRNA compared with bodies. After a 7 day exposure, there is distinct hybridization in the heads, but no signal is apparent in the bodies. Control experiments using actin as a probe showed that each lane on this Northern gel had approximately the same level of mRNA. The octopamine receptor mRNA is relatively rare, since the control actin hybridization was visible after a 1 hr exposure but the same gel required a 7 day exposure to see a signal for the receptor mRNA.

While the foregoing invention has been described in some detail for purposes of clarity and understanding, it will be appreciated by one skilled in the art from a reading of this disclosure that various changes in form and detail can be made without departing from the true scope of the invention and appended claims.

---

What is claimed is:

1. A naturally occurring invertebrate octopamine receptor protein encoded by SEQ ID NO: 1 or by a DNA sequence hybridizing to the complement of the sequence shown in SEQ ID NO: 1 under low stringency conditions, said octopamine receptor protein substantially free of proteins with which it is normally associated.

2. A recombinantly produced polypeptide comprising the amino acid sequence encoded by SEQ ID NO: 1 or a polypeptide encoded by a DNA sequence hybridizing to the complement of the sequence shown in SEQ ID NO: 1 under low stringency conditions, said sequence encoding a naturally occurring invertebrate octopamine receptor.

3. A method of testing a compound for its affinity for an invertebrate octopamine receptor, comprising:

contacting the membrane of a cell transformed with a polynucleotide with a labeled $\alpha_2$-adrenergic receptor antagonist in the presence and absence of said compound, said polynucleotide selected from the group consisting of a first polynucleotide encoding a naturally occurring invertebrate octopamine receptor protein comprising the amino acid sequence shown in SEQ ID NO: 2 and a second polynucleotide, said second polynucleotide capable of hybridizing to the complement of said first polynucleotide under low stringency hybridization conditions and which encodes a naturally occurring invertebrate octopamine receptor protein; and measuring the amount of labeled antagonist bound to said receptor in the presence of said compound versus in the absence of said compound.

4. A method of testing a compound for its ability to recognize an octopamine receptor, comprising:

incubating forskolin and said compound with control CHO-K1 cells and CHO-K1 cells, said cells transformed with the DNA sequence shown in SEQ ID NO: 1 or with a DNA sequence hybridizing to the complement of the sequence shown in SEQ ID NO: 1 under low stringency conditions and encoding a naturally occuring octopamine receptor; and measuring the increase or decrease of cAMP concentration in said control and transformed CHO-K1 cells.

5. The method of claim 4 wherein the receptor transfected CHO-K1 cells are Drosophila octopamine receptor transfected CHO-K1 cells.

* * * * *

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
( A ) LENGTH: 3335 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( i x ) FEATURE:
( A ) NAME/KEY: CDS
( B ) LOCATION: 319..2124

( x i ) SEQUENCE DESCRIPTION: SEQ ID NO:1:

```
GAATTCGTTC  TTGTGTAATA  AATAAATTGC  CAACAATTAT  AACTTGCAGT  CCACTCAGGC      60

ATATTCAAAT  GAAATGTGCC  ACAAAATGTT  TACGGTCATT  GCAACTCAAA  GCGACAGACC     120

ATAGACGAGG  TGCAAGGTGT  TGTGGCAGTT  GCAGAAAAAC  TAAAAGAAAG  CCGTAAGGCT     180

TGACCAAAAA  TTAATAACTG  ATAAAAGCAG  AAATAAGTCA  AAGAAGTCGG  GGAAATCGCA     240

CTCAACGTCC  GCCTTTCCAC  CAAGACGCAT  GTAAACGCAA  CCGGAGCCCA  AAGAAGGCAA     300

GTGGCAGGGC  AGGGAAAG ATG CCA TCG GCA GAT CAG ATC CTG TTT GTA AAT         351
                     Met Pro Ser Ala Asp Gln Ile Leu Phe Val Asn
                      1           5                    10

GTC ACC ACA ACG GTG GCG GCG GCG GCT CTA ACC GCT GCG GCC GCC GTC           399
Val Thr Thr Thr Val Ala Ala Ala Ala Leu Thr Ala Ala Ala Ala Val
             15                  20                  25

AGC ACC ACA AAG TCC GGA AAC GGC AAC GCC GCA CGG GGC TAC ACG GAT           447
```

-continued

| | | | | | | | | | | | | | | | | |
|---|---|---|---|---|---|---|---|---|---|---|---|---|---|---|---|---|
| Ser | Thr | Thr 30 | Lys | Ser | Gly | Asn | Gly 35 | Asn | Ala | Ala | Arg | Gly 40 | Tyr | Thr | Asp | |
| TCG | GAT | GAC | GAT | GCG | GGC | ATG | GGA | ACG | GAG | GCG | GTG | GCT | AAC | ATA | TCC | 495 |
| Ser | Asp 45 | Asp | Asp | Ala | Gly | Met 50 | Gly | Thr | Glu | Ala | Val 55 | Ala | Asn | Ile | Ser | |
| GGC | TCG | TGG | TGG | AGG | GCC | CTG | ACC | ACC | GTT | ACC | GCG | GCA | TTG | AGT | ACG | 543 |
| Gly 60 | Ser | Trp | Trp | Arg | Ala 65 | Leu | Thr | Thr | Val | Thr 70 | Ala | Ala | Leu | Ser | Thr 75 | |
| GCT | CAG | GCG | GAC | AAG | GAC | TCA | GCG | GGA | GAA | TGC | GAA | GGA | GCT | GTG | GAG | 591 |
| Ala | Gln | Ala | Asp | Lys 80 | Asp | Ser | Ala | Gly | Glu 85 | Cys | Glu | Gly | Ala | Val 90 | Glu | |
| GAG | CTG | CAT | GCC | AGC | ATC | CTG | GGC | CTC | CAG | CTG | GCT | GTG | CCG | GAG | TGG | 639 |
| Glu | Leu | His | Ala 95 | Ser | Ile | Leu | Gly | Leu 100 | Gln | Leu | Ala | Val | Pro 105 | Glu | Trp | |
| GAG | GCC | CTT | CTC | ACC | GCC | CTG | GTT | CTC | TCG | GTC | ATT | ATC | GTG | CTG | ACC | 687 |
| Glu | Ala | Leu 110 | Leu | Thr | Ala | Leu | Val 115 | Leu | Ser | Val | Ile | Ile 120 | Val | Leu | Thr | |
| ATC | ATC | GGG | AAC | ATC | CTG | GTG | ATT | CTG | AGT | GTG | TTC | ACC | TAC | AAG | CCG | 735 |
| Ile | Ile | Gly 125 | Asn | Ile | Leu | Val | Ile 130 | Leu | Ser | Val | Phe | Thr 135 | Tyr | Lys | Pro | |
| CTG | CGC | ATC | GTC | CAG | AAC | TTC | TTC | ATA | GTT | TCG | CTG | GCG | GTG | GCC | GAT | 783 |
| Leu 140 | Arg | Ile | Val | Gln | Asn 145 | Phe | Phe | Ile | Val | Ser 150 | Leu | Ala | Val | Ala | Asp 155 | |
| CTC | ACG | GTG | GCC | CTT | CTG | GTG | CTG | CCC | TTC | AAC | GTC | GCT | TAC | TCG | ATC | 831 |
| Leu | Thr | Val | Ala | Leu 160 | Leu | Val | Leu | Pro | Phe 165 | Asn | Val | Ala | Tyr | Ser 170 | Ile | |
| CTG | GGG | CGC | TGG | GAG | TTC | GGC | ATC | CAC | CTG | TGC | AAG | CTG | TGG | CTC | ACC | 879 |
| Leu | Gly | Arg | Trp 175 | Glu | Phe | Gly | Ile | His 180 | Leu | Cys | Lys | Leu | Trp 185 | Leu | Thr | |
| TGC | GAC | GTG | CTG | TGC | TGC | ACT | AGC | TCC | ATC | CTG | AAC | CCT | GTG | TGC | CAT | 927 |
| Cys | Asp | Val 190 | Leu | Cys | Cys | Thr | Ser 195 | Ser | Ile | Leu | Asn | Pro 200 | Val | Cys | His | |
| AGC | CCT | CGA | CCG | GTA | CTG | GGC | CAT | TAC | GGA | CCC | ATC | AAC | TAT | GCC | CAG | 975 |
| Ser | Pro 205 | Arg | Pro | Val | Leu | Gly 210 | His | Tyr | Gly | Pro | Ile 215 | Asn | Tyr | Ala | Gln | |
| AAG | AGG | ACC | GTT | GGT | CGC | GTC | CTG | CTC | CTC | ATC | TCC | GGG | GTG | TGG | CTA | 1023 |
| Lys 220 | Arg | Thr | Val | Gly | Arg 225 | Val | Leu | Leu | Leu | Ile 230 | Ser | Gly | Val | Trp | Leu 235 | |
| CTT | TCG | CTG | CTG | ATA | AGT | AGT | CCG | CCG | TTG | ATC | GGC | TGG | AAC | GAC | TGG | 1071 |
| Leu | Ser | Leu | Leu | Ile 240 | Ser | Ser | Pro | Pro | Leu 245 | Ile | Gly | Trp | Asn | Asp 250 | Trp | |
| CCG | GAC | GAG | TTC | ACA | AGC | GCC | ACG | CCC | TGC | GAG | CTG | ACC | TCG | CAG | CGA | 1119 |
| Pro | Asp | Glu | Phe 255 | Thr | Ser | Ala | Thr | Pro 260 | Cys | Glu | Leu | Thr | Ser 265 | Gln | Arg | |
| GGC | TAC | GTG | ATC | TAC | TCC | TCG | CTG | GGC | TCC | TTC | TTT | ATT | CCG | CTG | GCC | 1167 |
| Gly | Tyr | Val 270 | Ile | Tyr | Ser | Ser | Leu 275 | Gly | Ser | Phe | Phe | Ile 280 | Pro | Leu | Ala | |
| ATC | ATG | ACG | ATC | GTC | TAC | ATC | GAG | ATC | TTC | GTG | GCC | ACG | CGG | CGC | CGC | 1215 |
| Ile | Met | Thr 285 | Ile | Val | Tyr | Ile | Glu 290 | Ile | Phe | Val | Ala | Thr 295 | Arg | Arg | Arg | |
| CTA | AGG | GAG | CGA | GCC | AGG | GCC | AAC | AAG | CTT | AAC | ACG | ATC | GCT | CTG | AAG | 1263 |
| Leu 300 | Arg | Glu | Arg | Ala | Arg 305 | Ala | Asn | Lys | Leu | Asn 310 | Thr | Ile | Ala | Leu | Lys 315 | |
| TCC | ACT | GAG | CTC | GAG | CCG | ATG | GCA | AAC | TCC | TCG | CCC | GTC | GCC | GCC | TCC | 1311 |
| Ser | Thr | Glu | Leu | Glu 320 | Pro | Met | Ala | Asn | Ser 325 | Ser | Pro | Val | Ala | Ala 330 | Ser | |
| AAC | TCC | GGC | TCC | AAG | TCG | CGT | CTC | CTA | GCC | AGC | TGG | CTT | TGC | TGC | GGC | 1359 |
| Asn | Ser | Gly | Ser 335 | Lys | Ser | Arg | Leu | Leu 340 | Ala | Ser | Trp | Leu | Cys 345 | Cys | Gly | |

| | | | | | | | | | | | | | | | | |
|---|---|---|---|---|---|---|---|---|---|---|---|---|---|---|---|---|
| CGG | GAT | CGG | GCC | CAG | TTC | GCC | ACG | CCT | ATG | ATC | CAG | AAC | GAC | CAG | GAG | 1407 |
| Arg | Asp | Arg | Ala | Gln | Phe | Ala | Thr | Pro | Met | Ile | Gln | Asn | Asp | Gln | Glu | |
| | | 350 | | | | 355 | | | | | | 360 | | | | |
| AGC | ATC | AGC | AGT | GAA | ACC | CAC | CAG | CCG | CAG | GAT | TCC | TCC | AAA | GCG | GGT | 1455 |
| Ser | Ile | Ser | Ser | Glu | Thr | His | Gln | Pro | Gln | Asp | Ser | Ser | Lys | Ala | Gly | |
| | 365 | | | | | 370 | | | | | 375 | | | | | |
| CCC | CAT | GGC | AAC | AGC | GAT | CCC | CAA | CAG | CAG | CAC | GTG | GTC | GTG | CTG | GTC | 1503 |
| Pro | His | Gly | Asn | Ser | Asp | Pro | Gln | Gln | Gln | His | Val | Val | Val | Leu | Val | |
| 380 | | | | | 385 | | | | | 390 | | | | | 395 | |
| AAG | AAG | TCG | CGT | CGC | GCC | AAG | ACC | AAG | GAC | TCC | ATT | AAG | CAC | GGC | AAG | 1551 |
| Lys | Lys | Ser | Arg | Arg | Ala | Lys | Thr | Lys | Asp | Ser | Ile | Lys | His | Gly | Lys | |
| | | | | 400 | | | | | 405 | | | | | 410 | | |
| ACC | CGT | GGT | GGC | CGC | AAG | TCG | CAG | TCC | TCG | TCC | ACA | TGC | GAG | CCC | CAC | 1599 |
| Thr | Arg | Gly | Gly | Arg | Lys | Ser | Gln | Ser | Ser | Ser | Thr | Cys | Glu | Pro | His | |
| | | | 415 | | | | | 420 | | | | | 425 | | | |
| GGC | GAG | CAA | CAG | CTC | TTA | CCC | GCC | GGC | GGG | GAT | GGC | GGT | AGC | TGC | CAG | 1647 |
| Gly | Glu | Gln | Gln | Leu | Leu | Pro | Ala | Gly | Gly | Asp | Gly | Gly | Ser | Cys | Gln | |
| | | 430 | | | | | 435 | | | | | 440 | | | | |
| CCC | GGC | GGA | GGC | CAC | TCT | GGA | GGC | GGA | AAG | TCG | GAC | GCC | GAG | ATC | AGC | 1695 |
| Pro | Gly | Gly | Gly | His | Ser | Gly | Gly | Gly | Lys | Ser | Asp | Ala | Glu | Ile | Ser | |
| | 445 | | | | | 450 | | | | | 455 | | | | | |
| ACG | GAG | AGC | GGG | AGC | GAT | CCC | AAA | GGT | TGC | ATA | CAG | GTC | TGC | GTG | ACT | 1743 |
| Thr | Glu | Ser | Gly | Ser | Asp | Pro | Lys | Gly | Cys | Ile | Gln | Val | Cys | Val | Thr | |
| 460 | | | | | 465 | | | | | 470 | | | | | 475 | |
| CAG | GCG | GAC | GAG | CAA | ACG | TCC | CTA | AAG | CTG | ACC | CCG | CCG | CAA | TCC | TCG | 1791 |
| Gln | Ala | Asp | Glu | Gln | Thr | Ser | Leu | Lys | Leu | Thr | Pro | Pro | Gln | Ser | Ser | |
| | | | | 480 | | | | | 485 | | | | | 490 | | |
| ACG | GGA | GTC | GCT | GCC | GTT | TCT | GTC | ACT | CCG | TTG | CAG | AAG | AAG | ACT | AGT | 1839 |
| Thr | Gly | Val | Ala | Ala | Val | Ser | Val | Thr | Pro | Leu | Gln | Lys | Lys | Thr | Ser | |
| | | | | 495 | | | | | 500 | | | | | 505 | | |
| GGG | GTT | AAC | CAG | TTC | ATT | GAG | GAG | AAA | CAG | AAG | ATC | TCG | CTT | TCC | AAG | 1887 |
| Gly | Val | Asn | Gln | Phe | Ile | Glu | Glu | Lys | Gln | Lys | Ile | Ser | Leu | Ser | Lys | |
| | | 510 | | | | | 515 | | | | | 520 | | | | |
| GAG | CGG | CGA | GCG | GCT | CGC | ACC | CTG | GGC | ATC | ATC | ATG | GGC | GTG | TTC | GTC | 1935 |
| Glu | Arg | Arg | Ala | Ala | Arg | Thr | Leu | Gly | Ile | Ile | Met | Gly | Val | Phe | Val | |
| | 525 | | | | | 530 | | | | | 535 | | | | | |
| ATC | TGC | TGG | CTG | CCC | TTC | TTC | CTC | ATG | TAC | GTC | ATT | CTG | CCC | TTC | TGC | 1983 |
| Ile | Cys | Trp | Leu | Pro | Phe | Phe | Leu | Met | Tyr | Val | Ile | Leu | Pro | Phe | Cys | |
| 540 | | | | | 545 | | | | | 550 | | | | | 555 | |
| CAG | ACC | TGC | TGC | CCC | ACG | AAC | AAG | TTC | AAG | AAC | TTC | ATC | ACC | TGG | CTG | 2031 |
| Gln | Thr | Cys | Cys | Pro | Thr | Asn | Lys | Phe | Lys | Asn | Phe | Ile | Thr | Trp | Leu | |
| | | | | 560 | | | | | 565 | | | | | 570 | | |
| GGC | TAC | ATC | AAC | TCG | GGC | CTG | AAT | CCG | GTC | ATC | TAC | ACC | ATC | TTC | AAC | 2079 |
| Gly | Tyr | Ile | Asn | Ser | Gly | Leu | Asn | Pro | Val | Ile | Tyr | Thr | Ile | Phe | Asn | |
| | | | 575 | | | | | 580 | | | | | 585 | | | |
| CTG | GAC | TAC | CGC | CGG | GCC | TTC | AAG | CGA | CTT | CTG | GGC | CTG | AAT | TGAGGCTGGC | | 2131 |
| Leu | Asp | Tyr | Arg | Arg | Ala | Phe | Lys | Arg | Leu | Leu | Gly | Leu | Asn | | | |
| | | 590 | | | | | 595 | | | | | 600 | | | | |

| | | | | |
|---|---|---|---|---|
| TGGCGGGGGC | GGGTGGAAGA | TATAAACCGG | GCCAATCATG | GTTCGAGCGG | GAGAGCGTAC | 2191 |
| CTCAAAGTTT | GTGCCAAACT | TAAATGGTCG | TGTATGCGTT | CAGCGGAGAT | CTCAGTCTAT | 2251 |
| GTACAGTTGG | ACCCCCAGTT | GATGAACTTC | CGAGTTCAAC | TTCTCTAACA | CATATATACT | 2311 |
| TTCAAATGCC | TTCT.TGGTGA | ACTCATTTTG | AAGAAGTGGA | TGAATTTGGT | AAAGTGTAAT | 2371 |
| AGATTGAATA | TAATTTTTAA | TGTTTAACGT | TTCGGCAAAG | TGAAAAGCCC | CCACATTGGA | 2431 |
| AAGTCAAAGA | TGAGACTCGA | GTGTATATAT | AGTTTCAAAC | TAAGTTATTA | TTTCTAGCCG | 2491 |
| TAATTAAAAT | ACTTTCATTT | AGTTTTGAAC | ATTTTTTTAA | TATATTGTTG | TTTGGAATCG | 2551 |
| ATTGAGATGT | ACCACCACAT | TAAGCGTAGA | TTGTTCAATA | CTCATACTAA | AATGGGTTGT | 2611 |

-continued

```
GCTGCGATTA AAGTGAGGAT GTTGCCTCAA GGCACAGCTA CTAGGAAAAT CATAAAAATT   2671

ACATGGTAAA GAATTATACA TGCATTATAC TCCAGCTAAG TGGCATCCCA AACGAGAATA   2731

GCATCAAATT GAATTTAATA CAATTAAATT AAATGTTTAG CACAAAGAA  TTGTGGCAAC   2791

TTTCGTGTTT CACCCTAAGC GTATGGATAA CCAAAAAGGT GTTTGTTAAA TTAAATCTGC   2851

GTCAAGATAT GTAAGCAACT ACTAAGCTAA ATAATAACTT CCAAGAGAGA AACGTTTCT   2911

AGGCATTACT TTAACGATTT GTATTTATAT GTACTTTAAT TGTAGGTAAA CGATAAACCA   2971

CTATACCTAA TGTATACTTT CAAATACGCT TTGGACTATT TGTTAAATAA TTTAACGATT   3031

AATTGTTTTT ATGGCATAGC AACTATTGTG TTGAGTGGGC AGCTTAAAGC TAGCACATCG   3091

AAACTTACTT AAGGTAGATA AATGTTTAAC TGCACGTTAC GAAATGCAAC AGAGTTGGCG   3151

AAAGGACGTA ATTCAATGGA TGTGTTAACT CAAGTACATG CTATATCGAA AATGTATATC   3211

ACAATTTATG TCTTTTAACG ACGATGTACG ATAGTTTCAC TAATTATATT GTTTAACGAG   3271

AAAGAGCGAG CAAAGCGTAA ATGAAAACAA ATAAAAGACA CATTCGAATT AAAGTTAGGA   3331

ATTC                                                                 3335
```

( 2 ) INFORMATION FOR SEQ ID NO:2:

( i ) SEQUENCE CHARACTERISTICS:
        ( A ) LENGTH: 601 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Pro Ser Ala Asp Gln Ile Leu Phe Val Asn Val Thr Thr Thr Val
 1               5                  10                  15

Ala Ala Ala Ala Leu Thr Ala Ala Ala Val Ser Thr Thr Lys Ser
                20                  25                  30

Gly Asn Gly Asn Ala Ala Arg Gly Tyr Thr Asp Ser Asp Asp Ala
            35                  40                  45

Gly Met Gly Thr Glu Ala Val Ala Asn Ile Ser Gly Ser Trp Trp Arg
    50                  55                  60

Ala Leu Thr Thr Val Thr Ala Ala Leu Ser Thr Ala Gln Ala Asp Lys
65                  70                  75                  80

Asp Ser Ala Gly Glu Cys Glu Gly Ala Val Glu Glu Leu His Ala Ser
                85                  90                  95

Ile Leu Gly Leu Gln Leu Ala Val Pro Glu Trp Glu Ala Leu Leu Thr
                100                 105                 110

Ala Leu Val Leu Ser Val Ile Ile Val Leu Thr Ile Ile Gly Asn Ile
            115                 120                 125

Leu Val Ile Leu Ser Val Phe Thr Tyr Lys Pro Leu Arg Ile Val Gln
    130                 135                 140

Asn Phe Phe Ile Val Ser Leu Ala Val Ala Asp Leu Thr Val Ala Leu
145                 150                 155                 160

Leu Val Leu Pro Phe Asn Val Ala Tyr Ser Ile Leu Gly Arg Trp Glu
                165                 170                 175

Phe Gly Ile His Leu Cys Lys Leu Trp Leu Thr Cys Asp Val Leu Cys
            180                 185                 190

Cys Thr Ser Ser Ile Leu Asn Pro Val Cys His Ser Pro Arg Pro Val
    195                 200                 205

Leu Gly His Tyr Gly Pro Ile Asn Tyr Ala Gln Lys Arg Thr Val Gly
```

|     |     |     |     | 210 |     |     |     |     | 215 |     |     |     | 220 |     |     |
| --- | --- | --- | --- | --- | --- | --- | --- | --- | --- | --- | --- | --- | --- | --- | --- |
| Arg 225 | Val | Leu | Leu | Leu | Ile 230 | Ser | Gly | Val | Trp | Leu 235 | Leu | Ser | Leu | Leu | Ile 240 |
| Ser | Ser | Pro | Pro | Leu 245 | Ile | Gly | Trp | Asn | Asp 250 | Trp | Pro | Asp | Glu | Phe 255 | Thr |
| Ser | Ala | Thr | Pro 260 | Cys | Glu | Leu | Thr | Ser 265 | Gln | Arg | Gly | Tyr | Val 270 | Ile | Tyr |
| Ser | Ser | Leu 275 | Gly | Ser | Phe | Phe | Ile 280 | Pro | Leu | Ala | Ile | Met 285 | Thr | Ile | Val |
| Tyr | Ile 290 | Glu | Ile | Phe | Val | Ala 295 | Thr | Arg | Arg | Arg | Leu 300 | Arg | Glu | Arg | Ala |
| Arg 305 | Ala | Asn | Lys | Leu | Asn 310 | Thr | Ile | Ala | Leu | Lys 315 | Ser | Thr | Glu | Leu | Glu 320 |
| Pro | Met | Ala | Asn | Ser 325 | Ser | Pro | Val | Ala | Ala 330 | Ser | Asn | Ser | Gly | Ser 335 | Lys |
| Ser | Arg | Leu | Leu 340 | Ala | Ser | Trp | Leu | Cys 345 | Cys | Gly | Arg | Asp | Arg 350 | Ala | Gln |
| Phe | Ala | Thr 355 | Pro | Met | Ile | Gln | Asn 360 | Asp | Gln | Glu | Ser | Ile 365 | Ser | Ser | Glu |
| Thr | His 370 | Gln | Pro | Gln | Asp | Ser 375 | Ser | Lys | Ala | Gly | Pro 380 | His | Gly | Asn | Ser |
| Asp 385 | Pro | Gln | Gln | Gln | His 390 | Val | Val | Val | Leu | Val 395 | Lys | Lys | Ser | Arg | Arg 400 |
| Ala | Lys | Thr | Lys | Asp 405 | Ser | Ile | Lys | His | Gly 410 | Lys | Thr | Arg | Gly | Gly 415 | Arg |
| Lys | Ser | Gln | Ser 420 | Ser | Ser | Thr | Cys | Glu 425 | Pro | His | Gly | Glu | Gln 430 | Gln | Leu |
| Leu | Pro | Ala 435 | Gly | Gly | Asp | Gly | Gly 440 | Ser | Cys | Gln | Pro | Gly 445 | Gly | Gly | His |
| Ser | Gly 450 | Gly | Gly | Lys | Ser | Asp 455 | Ala | Glu | Ile | Ser | Thr 460 | Glu | Ser | Gly | Ser |
| Asp 465 | Pro | Lys | Gly | Cys | Ile 470 | Gln | Val | Cys | Val | Thr 475 | Gln | Ala | Asp | Glu | Gln 480 |
| Thr | Ser | Leu | Lys | Leu 485 | Thr | Pro | Pro | Gln | Ser 490 | Ser | Thr | Gly | Val | Ala 495 | Ala |
| Val | Ser | Val | Thr 500 | Pro | Leu | Gln | Lys | Lys 505 | Thr | Ser | Gly | Val | Asn 510 | Gln | Phe |
| Ile | Glu | Glu | Lys 515 | Gln | Lys | Ile | Ser | Leu 520 | Ser | Lys | Glu | Arg 525 | Arg | Ala | Ala |
| Arg | Thr 530 | Leu | Gly | Ile | Ile | Met 535 | Gly | Val | Phe | Val | Ile 540 | Cys | Trp | Leu | Pro |
| Phe 545 | Phe | Leu | Met | Tyr | Val 550 | Ile | Leu | Pro | Phe | Cys 555 | Gln | Thr | Cys | Cys | Pro 560 |
| Thr | Asn | Lys | Phe | Lys 565 | Asn | Phe | Ile | Thr | Trp 570 | Leu | Gly | Tyr | Ile | Asn 575 | Ser |
| Gly | Leu | Asn | Pro 580 | Val | Ile | Tyr | Thr | Ile 585 | Phe | Asn | Leu | Asp | Tyr 590 | Arg | Arg |
| Ala | Phe | Lys 595 | Arg | Leu | Leu | Gly | Leu 600 | Asn |   |   |   |   |   |   |   |

( 2 ) INFORMATION FOR SEQ ID NO:3:

( i ) SEQUENCE CHARACTERISTICS:
        ( A ) LENGTH: 515 amino acids (B) TYPE: amino acid
(C) STRANDEDNESS: single
(D) TOPOLOGY: linear (ii) MOLECULE TYPE: protein (iii) HYPOTHETICAL: NO (iv) ANTI-SENSE: NO (v) FRAGMENT TYPE: internal (xi) SEQUENCE DESCRIPTION: SEQ ID NO:3:

```
Met Asn Pro Asp Leu Asp Thr Gly His Asn Thr Ser Ala Pro Ala Gln
1               5                   10                  15

Trp Gly Glu Leu Lys Asp Ala Asn Phe Thr Gly Pro Asn Gln Thr Ser
            20                  25                  30

Ser Asn Ser Thr Leu Pro Gln Leu Asp Val Thr Arg Ala Ile Ser Val
        35                  40                      45

Gly Leu Val Leu Gly Ala Phe Ile Leu Phe Ala Ile Val Gly Asn Ile
    50                  55                  60

Leu Val Ile Leu Ser Val Ala Cys Asn Arg His Leu Arg Thr Pro Thr
65                      70                  75                  80

Asn Tyr Phe Ile Val Asn Leu Ala Ile Ala Asp Leu Leu Thr Ser Phe
                85                  90                      95

Thr Val Leu Pro Phe Ser Ala Thr Ile Glu Val Leu Gly Tyr Trp Val
            100                 105                 110

Leu Gly Arg Ile Phe Cys Asp Ile Trp Ala Ala Val Asp Val Leu Cys
            115                 120                 125

Cys Thr Ala Ser Ile Leu Ser Leu Cys Ala Ile Ser Ile Asp Arg Tyr
    130                 135                 140

Ile Gly Val Arg Tyr Ser Leu Gln Tyr Pro Thr Leu Val Thr Arg Arg
145                 150                 155                 160

Lys Ala Ile Leu Ala Leu Leu Ser Val Trp Val Leu Ser Thr Val Ile
                165                 170                 175

Ser Ile Gly Pro Leu Leu Gly Trp Lys Glu Pro Ala Pro Asn Asp Asp
            180                 185                 190

Lys Glu Cys Gly Val Thr Glu Glu Pro Phe Tyr Ala Leu Phe Ser Ser
        195                 200                 205

Leu Gly Ser Phe Tyr Ile Pro Leu Ala Val Ile Leu Val Met Tyr Cys
    210                 215                 220

Arg Val Tyr Ile Val Ala Lys Arg Thr Thr Lys Asn Leu Glu Ala Gly
225                 230                 235                 240

Val Met Lys Glu Met Ser Asn Ser Lys Glu Leu Thr Leu Arg Ile His
            245                 250                 255

Ser Lys Asn Phe His Glu Asp Thr Leu Ser Ser Thr Lys Ala Lys Gly
            260                 265                 270

His Asn Pro Arg Ser Ser Ile Ala Val Lys Leu Phe Lys Phe Ser Arg
        275                 280                 285

Glu Lys Lys Ala Ala Lys Thr Leu Gly Ile Val Val Gly Met Phe Ile
    290                 295                 300

Leu Cys Trp Leu Pro Phe Phe Ile Ala Leu Pro Leu Gly Ser Leu Phe
305                 310                 315                 320

Ser Thr Leu Lys Pro Pro Asp Ala Val Phe Lys Val Val Thr Trp Leu
            325                 330                 335

Gly Tyr Phe Asn Ser Cys Leu Asn Pro Ile Leu Tyr Pro Cys Ser Ser
            340                 345                 350
```

```
Lys  Glu  Phe  Lys  Arg  Ala  Phe  Met  Arg  Ile  Leu  Gly  Cys  Gln  Cys  Arg
          355                     360                    365

Ser  Gly  Arg  Arg  Arg  Arg  Arg  Arg  Arg  Leu  Gly  Ala  Cys  Ala  Tyr
     370                 375                    380

Thr  Tyr  Arg  Pro  Trp  Thr  Arg  Gly  Gly  Ser  Leu  Glu  Arg  Ser  Gln  Ser
385                      390                    395                         400

Arg  Lys  Asp  Ser  Leu  Asp  Asp  Ser  Gly  Ser  Cys  Met  Ser  Gly  Ser  Gln
               405                    410                         415

Arg  Thr  Leu  Pro  Ser  Ala  Ser  Pro  Ser  Pro  Gly  Tyr  Leu  Gly  Arg  Gly
               420                    425                    430

Ala  Gln  Pro  Pro  Leu  Glu  Leu  Cys  Ala  Tyr  Pro  Glu  Trp  Lys  Ser  Gly
          435                    440                    445

Ala  Leu  Leu  Ser  Leu  Pro  Glu  Pro  Pro  Gly  Arg  Arg  Gly  Arg  Leu  Asp
     450                    455                    460

Ser  Gly  Pro  Leu  Phe  Thr  Phe  Lys  Leu  Leu  Gly  Glu  Pro  Glu  Ser  Pro
465                      470                    475                         480

Gly  Thr  Glu  Gly  Asp  Ala  Ser  Asn  Gly  Gly  Cys  Asp  Ala  Thr  Thr  Asp
               485                    490                         495

Leu  Ala  Asn  Gly  Gln  Pro  Gly  Phe  Lys  Ser  Asn  Met  Pro  Leu  Ala  Pro
               500                    505                    510

Gly  His  Phe
          515
```

( 2 ) INFORMATION FOR SEQ ID NO:4:

( i ) SEQUENCE CHARACTERISTICS:
        ( A ) LENGTH: 461 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( x i ) SEQUENCE DESCRIPTION: SEQ ID NO:4:

```
Met  Ala  Ser  Pro  Ala  Leu  Ala  Ala  Ala  Leu  Ala  Val  Ala  Ala  Ala  Ala
1                   5                    10                        15

Gly  Pro  Asn  Ala  Ala  Gly  Ala  Gly  Glu  Arg  Gly  Ser  Gly  Gly  Val  Ala
               20                   25                        30

Asn  Ala  Ser  Gly  Ala  Ser  Trp  Gly  Pro  Pro  Arg  Gly  Gln  Tyr  Ser  Ala
          35                   40                   45

Gly  Ala  Val  Ala  Gly  Leu  Ala  Ala  Val  Val  Gly  Phe  Leu  Ile  Val  Phe
     50                       55                   60

Thr  Val  Val  Gly  Asn  Val  Leu  Val  Val  Ile  Ala  Val  Leu  Thr  Ser  Arg
65                       70                   75                        80

Ala  Leu  Arg  Ala  Pro  Gln  Asn  Leu  Phe  Leu  Val  Ser  Leu  Ala  Ser  Ala
               85                   90                        95

Asp  Ile  Leu  Val  Ala  Thr  Leu  Val  Met  Pro  Phe  Ser  Leu  Ala  Asn  Glu
               100                  105                       110

Leu  Met  Ala  Tyr  Trp  Tyr  Phe  Gly  Gln  Val  Trp  Cys  Gly  Val  Tyr  Leu
          115                      120                  125

Ala  Leu  Asp  Val  Leu  Phe  Cys  Thr  Ser  Ser  Ile  Val  His  Leu  Cys  Ala
     130                       135                  140
```

```
Ile  Ser  Leu  Asp  Arg  Tyr  Trp  Ser  Val  Thr  Gly  Ala  Val  Glu  Tyr  Asn
145                 150                 155                           160

Leu  Lys  Arg  Thr  Pro  Arg  Arg  Val  Lys  Ala  Thr  Ile  Val  Ala  Val  Trp
                165                 170                           175

Ile  Ile  Ser  Ala  Val  Ile  Ser  Phe  Pro  Pro  Leu  Val  Ser  Leu  Tyr  Arg
                180                 185                      190

Gln  Pro  Asp  Gly  Ala  Ala  Tyr  Pro  Gln  Cys  Gly  Leu  Asn  Asp  Glu  Thr
          195                 200                      205

Trp  Tyr  Ile  Leu  Ser  Ser  Cys  Ile  Gln  Ser  Phe  Phe  Ala  Pro  Cys  Leu
          210                 215                      220

Ile  Met  Gly  Leu  Val  Tyr  Ala  Arg  Ile  Tyr  Arg  Val  Ala  Lys  Arg  Arg
225                 230                 235                           240

Thr  Arg  Thr  Leu  Ser  Glu  Lys  Arg  Ala  Pro  Val  Gly  Pro  Asp  Gly  Ala
                245                 250                      255

Ser  Pro  Thr  Thr  Glu  Asn  Gly  Leu  Gly  Ala  Ala  Ala  Gly  Glu  Ala  Arg
                260            265                      270

Thr  Gly  Thr  Ala  Arg  Pro  Arg  Pro  Pro  Thr  Trp  Ala  Arg  Thr  Arg  Ala
                275            280                      285

Ala  Gln  Arg  Pro  Arg  Gly  Gly  Ala  Pro  Gly  Pro  Leu  Arg  Arg  Gly  Gly
          290                 295                      300

Arg  Arg  Arg  Ala  Gly  Ala  Glu  Gly  Gly  Ala  Gly  Gly  Ala  Asp  Gly  Gln
305                 310                      315                      320

Gly  Ala  Gly  Pro  Gly  Ala  Ala  Gln  Ser  Gly  Ala  Leu  Thr  Ala  Ser  Arg
                325                 330                      335

Ser  Pro  Gly  Pro  Gly  Gly  Arg  Leu  Ser  Arg  Ala  Ser  Ser  Arg  Ser  Val
                340                 345                      350

Glu  Phe  Phe  Leu  Ser  Arg  Arg  Arg  Ala  Arg  Ser  Ser  Val  Cys  Arg
          355                 360                      365

Arg  Lys  Val  Ala  Gln  Ala  Arg  Glu  Lys  Arg  Phe  Thr  Phe  Val  Leu  Ala
          370                 375                      380

Val  Val  Met  Gly  Val  Phe  Val  Leu  Cys  Trp  Phe  Pro  Phe  Phe  Phe  Ile
385                 390                      395                      400

Tyr  Ser  Leu  Tyr  Gly  Ile  Cys  Arg  Glu  Ala  Cys  Gln  Val  Pro  Gly  Pro
                405                 410                      415

Leu  Phe  Lys  Phe  Phe  Phe  Trp  Ile  Gly  Tyr  Cys  Asn  Ser  Ser  Ile  Asn
                420                 425                      430

Pro  Val  Leu  Tyr  Thr  Val  Phe  Asn  Gln  Asp  Phe  Arg  Ala  Ser  Phe  Lys
          435                 440                      445

His  Ile  Leu  Phe  Arg  Arg  Arg  Arg  Gly  Phe  Arg  Gln
     450                 455                 460
```

( 2 ) INFORMATION FOR SEQ ID NO:5:

( i ) SEQUENCE CHARACTERISTICS:
        ( A ) LENGTH: 450 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( x i ) SEQUENCE DESCRIPTION: SEQ ID NO:5:

| Ser | Gln | Ser | Leu | Gln | Pro | Asp | Ala | Gly | Asn | Ala | Ser | Trp | Asn | Gly | Thr |
| 1 | | | | 5 | | | | | 10 | | | | | 15 | |
| Glu | Ala | Pro | Gln | Gln | Gln | Ala | Arg | Ala | Thr | Pro | Tyr | Ser | Leu | Gln | Val |
| | | | 20 | | | | 25 | | | | | | 30 | | |
| Thr | Leu | Thr | Leu | Val | Cys | Leu | Ala | Gly | Leu | Leu | Met | Leu | Leu | Thr | Val |
| | | 35 | | | | 40 | | | | | 45 | | | | |
| Phe | Gly | Asn | Val | Leu | Val | Ile | Ile | Ala | Val | Phe | Thr | Ser | Arg | Ala | Leu |
| | 50 | | | | | 55 | | | | | 60 | | | | |
| Lys | Ala | Pro | Gln | Asn | Leu | Phe | Leu | Val | Ser | Leu | Ala | Ser | Ala | Asp | Ile |
| 65 | | | | | 70 | | | | | 75 | | | | | 80 |
| Leu | Val | Ala | Thr | Leu | Val | Ile | Pro | Phe | Ser | Leu | Ala | Asn | Glu | Val | Met |
| | | | | 85 | | | | | 90 | | | | | 95 | |
| Gly | Tyr | Trp | Tyr | Phe | Gly | Lys | Thr | Trp | Cys | Glu | Ile | Tyr | Leu | Ala | Leu |
| | | | 100 | | | | 105 | | | | | | 110 | | |
| Asp | Val | Leu | Phe | Cys | Thr | Ser | Ser | Ile | Val | His | Leu | Cys | Ala | Ile | Ser |
| | | 115 | | | | 120 | | | | | 125 | | | | |
| Leu | Asp | Arg | Tyr | Trp | Ser | Ile | Thr | Gln | Ala | Ile | Glu | Tyr | Asn | Leu | Lys |
| | 130 | | | | | 135 | | | | | 140 | | | | |
| Arg | Thr | Pro | Arg | Arg | Ile | Lys | Ala | Ile | Leu | Ile | Thr | Val | Trp | Val | Ile |
| 145 | | | | | 150 | | | | | 155 | | | | | 160 |
| Ser | Ala | Val | Ile | Ser | Phe | Pro | Pro | Leu | Ile | Ser | Ile | Glu | Lys | Lys | Gly |
| | | | | 165 | | | | | 170 | | | | | 175 | |
| Gly | Gly | Gly | Gly | Pro | Gln | Pro | Ala | Glu | Pro | Arg | Cys | Glu | Ile | Asn | Asp |
| | | | 180 | | | | 185 | | | | | | 190 | | |
| Gln | Lys | Trp | Tyr | Val | Ile | Ala | Ser | Cys | Ile | Gly | Ser | Phe | Phe | Ala | Pro |
| | | 195 | | | | 200 | | | | | 205 | | | | |
| Cys | Leu | Ile | Met | Ile | Leu | Val | Tyr | Val | Arg | Ile | Tyr | Gln | Ile | Ala | Lys |
| | 210 | | | | | 215 | | | | | 220 | | | | |
| Arg | Arg | Thr | Arg | Val | Pro | Pro | Ser | Arg | Arg | Gly | Pro | Asp | Ala | Val | Ala |
| 225 | | | | | 230 | | | | | 235 | | | | | 240 |
| Ala | Pro | Pro | Gly | Gly | Thr | Glu | Arg | Arg | Pro | Asn | Gly | Leu | Gly | Pro | Glu |
| | | | | 245 | | | | | 250 | | | | | 255 | |
| Arg | Ser | Ala | Gly | Pro | Gly | Gly | Ala | Glu | Ala | Glu | Pro | Leu | Pro | Thr | Gln |
| | | | 260 | | | | 265 | | | | | | 270 | | |
| Leu | Asn | Gly | Ala | Pro | Gly | Glu | Pro | Ala | Pro | Ala | Gly | Pro | Arg | Asp | Thr |
| | | 275 | | | | 280 | | | | | 285 | | | | |
| Asp | Ala | Leu | Asp | Leu | Glu | Glu | Ser | Ser | Ser | Asp | His | Ala | Glu | Arg |
| | 290 | | | | | 295 | | | | | 300 | | | | |
| Pro | Pro | Gly | Pro | Arg | Arg | Pro | Glu | Arg | Gly | Pro | Arg | Gly | Lys | Gly | Lys |
| 305 | | | | | 310 | | | | | 315 | | | | | 320 |
| Ala | Arg | Ala | Ser | Gln | Val | Lys | Pro | Gly | Asp | Ser | Leu | Arg | Gly | Ala | Gly |
| | | | | 325 | | | | | 330 | | | | | 335 | |
| Arg | Gly | Arg | Arg | Gly | Ser | Gly | Arg | Arg | Leu | Gln | Gly | Arg | Gly | Arg | Ser |
| | | | 340 | | | | 345 | | | | | | 350 | | |
| Ala | Ser | Gly | Leu | Pro | Arg | Arg | Arg | Ala | Gly | Ala | Gln | Gly | Gln | Asn | Arg |
| | | 355 | | | | 360 | | | | | 365 | | | | |
| Glu | Lys | Arg | Phe | Thr | Phe | Val | Leu | Ala | Val | Val | Ile | Gly | Val | Phe | Val |
| | 370 | | | | | 375 | | | | | 380 | | | | |
| Val | Cys | Trp | Phe | Pro | Phe | Phe | Phe | Thr | Tyr | Thr | Leu | Thr | Ala | Val | Gly |
| 385 | | | | | 390 | | | | | 395 | | | | | 400 |
| Cys | Ser | Val | Pro | Arg | Thr | Leu | Phe | Lys | Phe | Phe | Phe | Trp | Phe | Gly | Tyr |
| | | | | 405 | | | | | 410 | | | | | 415 | |

-continued

```
Cys  Asn  Ser  Ser  Leu  Asn  Pro  Val  Ile  Tyr  Thr  Ile  Phe  Asn  His  Asp
               420                      425                     430

Phe  Arg  Arg  Ala  Phe  Lys  Lys  Ile  Leu  Cys  Arg  Gly  Asp  Arg  Lys  Arg
               435                      440                     445

Ile  Val
     450
```

( 2 ) INFORMATION FOR SEQ ID NO:6:

( i ) SEQUENCE CHARACTERISTICS:
        ( A ) LENGTH: 472 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( x i ) SEQUENCE DESCRIPTION: SEQ ID NO:6:

```
Met  Gly  Ala  Gly  Val  Leu  Val  Leu  Gly  Ala  Ser  Glu  Pro  Gly  Asn  Leu
1                    5                       10                      15

Ser  Ser  Ala  Ala  Pro  Leu  Pro  Asp  Gly  Ala  Ala  Thr  Ala  Ala  Arg  Leu
               20                       25                      30

Leu  Val  Pro  Ala  Ser  Pro  Pro  Ala  Ser  Leu  Leu  Pro  Pro  Ala  Ser  Glu
          35                       40                      45

Ser  Pro  Glu  Pro  Leu  Ser  Gln  Gln  Trp  Thr  Ala  Gly  Met  Gly  Leu  Leu
     50                      55                      60

Met  Ala  Leu  Ile  Val  Leu  Leu  Ile  Val  Ala  Gly  Asn  Val  Leu  Val  Ile
65                       70                      75                          80

Val  Ala  Ile  Ala  Lys  Thr  Pro  Arg  Leu  Gln  Thr  Leu  Thr  Asn  Leu  Phe
               85                       90                      95

Ile  Met  Ser  Leu  Ala  Ser  Ala  Asp  Ile  Val  Met  Gly  Leu  Leu  Val  Val
               100                      105                     110

Pro  Phe  Gly  Ala  Thr  Ile  Val  Val  Trp  Gly  Arg  Trp  Glu  Tyr  Gly  Ser
          115                      120                     125

Phe  Phe  Cys  Glu  Leu  Trp  Thr  Ser  Val  Asp  Val  Leu  Cys  Val  Thr  Ala
     130                      135                     140

Ser  Ile  Glu  Thr  Leu  Cys  Val  Ile  Ala  Leu  Asp  Arg  Tyr  Leu  Ala  Ile
145                      150                     155                         160

Thr  Ser  Pro  Phe  Arg  Tyr  Gln  Ser  Leu  Leu  Thr  Arg  Ala  Arg  Ala  Arg
               165                      170                     175

Gly  Leu  Val  Cys  Thr  Val  Trp  Ala  Ile  Ser  Ala  Leu  Val  Ser  Phe  Leu
               180                      185                     190

Pro  Ile  Leu  Met  His  Trp  Trp  Arg  Ala  Glu  Ser  Asp  Glu  Ala  Arg  Arg
          195                      200                     205

Cys  Tyr  Asn  Asp  Pro  Lys  Cys  Cys  Asp  Phe  Val  Thr  Asn  Arg  Ala  Tyr
     210                      215                     220

Ala  Ile  Ala  Ser  Ser  Val  Val  Ser  Phe  Tyr  Val  Pro  Ile  Cys  Ile  Met
225                      230                     235                         240

Ala  Phe  Val  Tyr  Leu  Arg  Val  Phe  Arg  Glu  Ala  Gln  Lys  Gln  Val  Lys
               245                      250                     255

Arg  Arg  Phe  Leu  Gly  Gly  Pro  Ala  Arg  Pro  Pro  Ser  Pro  Ser  Pro  Ser
               260                      265                     270
```

```
Pro  Val  Pro  Ala  Pro  Ala  Pro  Pro  Pro  Gly  Pro  Pro  Arg  Pro  Ala  Ala
     275                      280                 285

Leu  Pro  Gln  His  Gln  Pro  Ile  Leu  Gly  Asn  Gly  Arg  Ala  Gly  Lys  Arg
     290                      295                 300

Arg  Pro  Ser  Arg  Leu  Val  Ala  Leu  Glu  Glu  Gln  Lys  Ala  Leu  Lys  Thr
305                      310                 315                           320

Leu  Gly  Ile  Leu  Met  Gly  Val  Phe  Thr  Leu  Cys  Trp  Leu  Pro  Phe  Phe
               325                      330                           335

Leu  Ala  Asn  Val  Val  Lys  Ala  Phe  His  Arg  Glu  Leu  Val  Pro  Asp  Arg
               340                      345                           350

Leu  Phe  Val  Phe  Phe  Asn  Trp  Leu  Gly  Tyr  Ala  Asn  Ser  Ala  Phe  Asn
          355                      360                 365

Pro  Ile  Leu  Tyr  Cys  Arg  Ser  Pro  Asp  Phe  Arg  Lys  Ala  Phe  Gln  Cys
     370                      375                 380

Leu  Leu  Cys  Cys  Ala  Arg  Arg  Ala  Ala  Arg  Arg  Arg  His  Ala  Thr  His
385                      390                 395                           400

Gly  Asp  Arg  Pro  Arg  Ala  Ser  Gly  Cys  Leu  Ala  Arg  Pro  Cys  Pro  Pro
               405                      410                           415

Pro  Ser  Pro  Cys  Ala  Ala  Ser  Asp  Asp  Asp  Asp  Asp  Val  Val  Cys
               420                      425                 430

Ala  Thr  Pro  Pro  Ala  Arg  Leu  Leu  Glu  Pro  Trp  Ala  Gly  Cys  Asn  Gly
          435                      440                 445

Cys  Ala  Ala  Ala  Asp  Ser  Asp  Ser  Ser  Leu  Asp  Glu  Pro  Cys  Arg  Pro
     450                      455                 460

Gly  Phe  Ala  Ser  Glu  Ser  Lys  Val
465                      470
```

( 2 ) INFORMATION FOR SEQ ID NO:7:

( i ) SEQUENCE CHARACTERISTICS:
        ( A ) LENGTH: 483 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( x i ) SEQUENCE DESCRIPTION: SEQ ID NO:7:

```
Met  Gly  Asp  Gln  Trp  Leu  Pro  Pro  Asp  Cys  Gly  Pro  His  Asn  Arg  Ser
1                   5                   10                            15

Gly  Gly  Gly  Gly  Ala  Thr  Ala  Ala  Pro  Thr  Gly  Ser  Arg  Gln  Val  Ser
               20                      25                  30

Ala  Glu  Leu  Leu  Ser  Gln  Gln  Trp  Glu  Ala  Gly  Met  Ser  Leu  Leu  Met
               35                      40                  45

Ala  Leu  Val  Val  Leu  Leu  Ile  Val  Ala  Gly  Asn  Val  Leu  Val  Ile  Ala
     50                      55                  60

Ala  Ile  Gly  Arg  Thr  Gln  Arg  Leu  Gly  Thr  Leu  Thr  Asn  Leu  Phe  Ile
65                      70                  75                           80

Thr  Ser  Leu  Ala  Cys  Ala  Asp  Ile  Val  Met  Gly  Leu  Leu  Val  Val  Pro
               85                      90                           95

Phe  Gly  Ala  Thr  Ile  Val  Val  Arg  Gly  Thr  Trp  Leu  Trp  Gly  Ser  Phe
               100                     105                          110
```

| | | | | | | | | | | | | | | |
|---|---|---|---|---|---|---|---|---|---|---|---|---|---|---|
| Leu | Cys | Glu 115 | Cys | Trp | Thr | Ser | Leu 120 | Asp | Val | Leu | Cys 125 | Val | Thr | Ala | Ser |
| Ile | Glu 130 | Thr | Leu | Cys | Val 135 | Ile | Ala | Ile | Asp | Arg | Tyr 140 | Leu | Ala | Ile | Thr |
| Ser 145 | Pro | Phe | Arg | Tyr | Gln 150 | Ser | Leu | Met | Thr | Arg 155 | Ala | Arg | Ala | Lys | Val 160 |
| Ile | Ile | Cys | Thr | Val 165 | Trp | Ala | Ile | Ser | Ala 170 | Leu | Val | Ser | Phe | Leu 175 | Pro |
| Ile | Met | Met | His 180 | Trp | Trp | Arg | Asp | Glu 185 | Asp | Pro | Gln | Ala | Leu 190 | Lys | Cys |
| Tyr | Gln | Asp 195 | Pro | Gly | Cys | Cys | Asp 200 | Phe | Val | Thr | Asn | Arg 205 | Ala | Tyr | Ala |
| Ile | Ala | Ser 210 | Ser | Ile | Ile | Ser 215 | Phe | Tyr | Ile | Pro | Leu 220 | Leu | Ile | Met | Ile |
| Phe 225 | Val | Tyr | Leu | Arg | Val 230 | Tyr | Arg | Glu | Ala | Lys 235 | Glu | Gln | Ile | Arg | Lys 240 |
| Ile | Asp | Arg | Cys | Glu 245 | Gly | Arg | Phe | Tyr | Gly 250 | Ser | Gln | Glu | Gln | Pro 255 | Gln |
| Pro | Pro | Pro | Pro 260 | Asn | Leu | Gly | Gln | Val 265 | Glu | Gln | Asp | Asn | Gly 270 | Arg | Ala |
| Ser | Lys | Arg 275 | Lys | Thr | Ser | Arg | Val 280 | Met | Ala | Met | Arg | Glu 285 | His | Lys | Ala |
| Leu | Lys 290 | Thr | Leu | Gln | Ile | Ile 295 | Met | Gly | Val | Phe | Thr 300 | Leu | Cys | Trp | Leu |
| Pro 305 | Phe | Phe | Leu | Val | Asn 310 | Ile | Val | Asn | Val | Phe 315 | Asn | Arg | Asp | Leu | Val 320 |
| Pro | Asp | Trp | Leu | Phe 325 | Val | Phe | Phe | Asn | Trp 330 | Leu | Gly | Tyr | Ala | Asn 335 | Ser |
| Ala | Phe | Asn | Pro 340 | Ile | Ile | Tyr | Cys | Arg 345 | Ser | Pro | Asp | Phe | Arg 350 | Lys | Ala |
| Phe | Lys | Arg 355 | Leu | Leu | Cys | Phe | Pro 360 | Arg | Lys | Ala | Asp | Arg 365 | Arg | Leu | His |
| Ala | Gly 370 | Gly | Gln | Pro | Ala | Pro 375 | Leu | Pro | Gly | Gly | Phe 380 | Ile | Ser | Thr | Leu |
| Gly 385 | Ser | Pro | Glu | His | Ser 390 | Pro | Gly | Gly | Thr | Trp 395 | Ser | Asp | Cys | Asn | Gly 400 |
| Gly | Thr | Arg | Gly | Gly 405 | Ser | Glu | Ser | Ser | Leu 410 | Glu | Glu | Arg | His | Ser 415 | Lys |
| Thr | Ser | Arg | Ser 420 | Glu | Ser | Lys | Met | Glu 425 | Arg | Glu | Lys | Asn | Ile 430 | Leu | Ala |
| Thr | Thr | Arg 435 | Phe | Tyr | Cys | Thr | Phe 440 | Leu | Gly | Asn | Gly | Asp 445 | Lys | Ala | Val |
| Phe | Cys 450 | Thr | Val | Leu | Arg | Ile 455 | Val | Lys | Leu | Phe | Glu 460 | Asp | Ala | Thr | Cys |
| Thr 465 | Cys | Pro | His | Thr | His 470 | Leu | Lys | Leu | Met | Lys 475 | Trp | Arg | Phe | Lys | Gln 480 |
| His | Gly | Ala | | | | | | | | | | | | | |

( 2 ) INFORMATION FOR SEQ ID NO:8:

( i ) SEQUENCE CHARACTERISTICS:
        ( A ) LENGTH: 417 amino acids
        ( B ) TYPE: amino acid
        ( C ) STRANDEDNESS: single
        ( D ) TOPOLOGY: linear (i i) MOLECULE TYPE: protein (i i i) HYPOTHETICAL: NO (i v) ANTI-SENSE: NO (v) FRAGMENT TYPE: internal (x i) SEQUENCE DESCRIPTION: SEQ ID NO:8:

```
Met Gly Pro Pro Gly Asn Asp Ser Asp Phe Leu Leu Thr Thr Asn Gly
 1               5                  10                  15

Ser His Val Pro Asp His Asp Val Thr Glu Glu Arg Asp Glu Ala Trp
                20                  25                  30

Val Val Gly Met Ala Ile Leu Met Ser Val Ile Val Leu Ala Ile Val
            35                  40                  45

Phe Gly Asn Val Leu Val Ile Thr Ala Ile Ala Lys Phe Glu Arg Leu
    50                  55                  60

Gln Thr Val Thr Asn Tyr Phe Ile Ser Leu Ala Cys Ala Asp Leu Val
 65                  70                  75                  80

Met Gly Leu Ala Val Val Pro Phe Gly Ala Ser His Ile Leu Met Lys
                85                  90                  95

Met Trp Asn Phe Gly Asn Phe Trp Cys Glu Phe Trp Thr Ser Ile Asp
            100                 105                 110

Val Leu Cys Val Thr Ala Ser Ile Glu Thr Leu Cys Val Ile Ala Val
        115                 120                 125

Asp Arg Tyr Ile Ala Ile Thr Ser Pro Phe Lys Val Gln Ser Leu Leu
    130                 135                 140

Thr Lys Asn Lys Ala Arg Met Val Ile Leu Met Val Trp Ile Val Ser
145                 150                 155                 160

Gln Leu Thr Ser Phe Ile Pro Ile Gln Met His Trp Tyr Arg Ala Thr
                165                 170                 175

His Gln Lys Ala Ile Asp Cys Tyr His Lys Glu Thr Cys Cys Asp Phe
            180                 185                 190

Phe Thr Asn Gln Ala Tyr Ala Ile Ala Ser Ser Ile Val Ser Phe Tyr
        195                 200                 205

Val Pro Leu Val Val Met Val Phe Val Tyr Ser Arg Val Phe Gln Val
    210                 215                 220

Ala Lys Arg Gln Leu Gln Lys Ile Asp Lys Ser Glu Gly Arg Phe His
225                 230                 235                 240

Ser Pro Asn Leu Gln Gln Val Glu Gln Asp Gly Arg Ser Gly His Gly
                245                 250                 255

Leu Arg Arg Ser Ser Lys Phe Cys Leu Lys Glu His Lys Ala Leu Lys
            260                 265                 270

Thr Leu Gln Ile Ile Met Gly Thr Phe Thr Leu Cys Trp Leu Pro Phe
        275                 280                 285

Phe Ile Val Asn Ile Val His Val Ile Gln Asp Asn Leu Ile Pro Lys
    290                 295                 300

Glu Val Tyr Ile Leu Leu Asn Trp Leu Gly Tyr Val Asn Ser Ala Phe
305                 310                 315                 320

Asn Pro Leu Ile Tyr Cys Arg Ser Pro Asp Phe Arg Ile Ala Phe Gln
                325                 330                 335

Glu Leu Leu Cys Leu Arg Arg Ser Ser Lys Ala Tyr Gly Asn Gly
            340                 345                 350

Tyr Ser Ser Asn Ser Asn Gly Lys Thr Asp Tyr Met Gly Glu Ala Ser
        355                 360                 365
```

```
            Gly  Cys  Gln  Leu  Gly  Gln  Glu  Lys  Glu  Ser  Glu  Arg  Leu  Cys  Glu  Asp
                 370                 375                 380

Pro  Pro  Gly  Thr  Glu  Ser  Phe  Val  Asn  Cys  Gln  Gly  Thr  Val  Pro  Ser
            385                 390                 395                                400

Leu  Ser  Leu  Asp  Ser  Gln  Gly  Arg  Asn  Cys  Ser  Thr  Asn  Asp  Ser  Pro
                                405                 410                 415

Leu
```

( 2 ) INFORMATION FOR SEQ ID NO:9:

( i ) SEQUENCE CHARACTERISTICS:
        ( A ) LENGTH: 418 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( x i ) SEQUENCE DESCRIPTION: SEQ ID NO:9:

```
            Met  Glu  Pro  His  Gly  Asn  Asp  Ser  Asp  Phe  Leu  Leu  Ala  Pro  Asn  Gly
            1                    5                   10                  15

Ser  Arg  Ala  Pro  Gly  His  Asp  Ile  Thr  Gln  Glu  Arg  Asp  Glu  Ala  Trp
                           20                  25                  30

Val  Val  Gly  Met  Ala  Ile  Leu  Met  Ser  Val  Ile  Val  Leu  Ala  Ile  Val
                           35                  40                  45

Phe  Gly  Asn  Val  Leu  Val  Ile  Thr  Ala  Ile  Ala  Lys  Phe  Glu  Arg  Leu
                 50                       55                  60

Gln  Thr  Val  Thr  Asn  Tyr  Phe  Ile  Thr  Ser  Leu  Ala  Cys  Ala  Asp  Leu
            65                       70                  75                            80

Val  Met  Gly  Leu  Ala  Val  Val  Pro  Phe  Gln  Ala  Ser  His  Ile  Leu  Met
                                85                       90                       95

Lys  Met  Trp  Asn  Phe  Gly  Asn  Phe  Trp  Cys  Glu  Phe  Trp  Thr  Ser  Ile
                           100                      105                      110

Asp  Val  Leu  Cys  Val  Thr  Ala  Ser  Ile  Glu  Thr  Leu  Cys  Val  Ile  Ala
                           115                      120                      125

Val  Asp  Arg  Tyr  Val  Ala  Ile  Thr  Ser  Pro  Phe  Lys  Tyr  Gln  Ser  Leu
                 130                      135                      140

Leu  Thr  Lys  Asn  Lys  Ala  Arg  Val  Val  Ile  Leu  Met  Val  Trp  Ile  Val
            145                      150                      155                      160

Ser  Gly  Leu  Thr  Ser  Phe  Leu  Pro  Ile  Gln  Met  His  Trp  Tyr  Arg  Ala
                                165                      170                      175

Thr  His  Lys  Gln  Ala  Ile  Asp  Cys  Tyr  Ala  Lys  Glu  Thr  Cys  Cys  Asp
                           180                      185                      190

Phe  Phe  Thr  Asn  Gln  Ala  Tyr  Ala  Ile  Ala  Ser  Ser  Ile  Val  Ser  Phe
                           195                      200                      205

Tyr  Val  Pro  Leu  Val  Val  Met  Val  Phe  Val  Tyr  Ser  Arg  Val  Phe  Gln
                 210                      215                      220

Val  Ala  Lys  Arg  Gln  Leu  Gln  Lys  Ile  Asp  Lys  Ser  Glu  Gly  Arg  Phe
            225                      230                      235                      240

His  Ala  Gln  Asn  Leu  Ser  Gln  Val  Glu  Gln  Asp  Gly  Arg  Ser  Gly  His
                                245                      250                      255
```

```
Gly  Leu  Arg  Ser  Ser  Ser  Lys  Phe  Cys  Leu  Lys  Glu  His  Lys  Ala  Leu
               260                 265                 270

Lys  Thr  Leu  Gly  Ile  Ile  Met  Gly  Thr  Phe  Thr  Leu  Cys  Trp  Leu  Pro
          275                 280                 285

Phe  Phe  Ile  Val  Asn  Ile  Val  His  Val  Ile  Arg  Ala  Asn  Leu  Ile  Pro
     290                 295                      300

Lys  Glu  Val  Tyr  Ile  Ile  Leu  Asn  Trp  Leu  Gly  Tyr  Val  Asn  Ser  Ala
305                      310                 315                           320

Phe  Asn  Pro  Ile  Ile  Tyr  Cys  Arg  Ser  Pro  Asp  Phe  Arg  Ile  Ala  Phe
                    325                 330                           335

Gln  Glu  Leu  Leu  Cys  Leu  Arg  Arg  Ser  Ser  Lys  Thr  Tyr  Gly  Asn
               340                 345                      350

Gly  Tyr  Ser  Ser  Asn  Ser  Asn  Gly  Arg  Thr  Asp  Tyr  Thr  Gly  Glu  Gln
          355                      360                 365

Ser  Ala  Tyr  Gln  Leu  Gly  Gln  Glu  Lys  Glu  Asn  Glu  Leu  Leu  Cys  Glu
     370                 375                 380

Glu  Ala  Pro  Gly  Met  Glu  Gly  Phe  Val  Asn  Cys  Gln  Gly  Thr  Val  Pro
385                      390                 395                           400

Ser  Leu  Ser  Ile  Asp  Ser  Gln  Gly  Arg  Asn  Cys  Asn  Thr  Asn  Asp  Ser
               405                      410                      415

Pro  Leu
```

( 2 ) INFORMATION FOR SEQ ID NO:10:

( i ) SEQUENCE CHARACTERISTICS:
        ( A ) LENGTH: 415 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( x i ) SEQUENCE DESCRIPTION: SEQ ID NO:10:

```
Met  Asp  Pro  Leu  Asn  Leu  Ser  Trp  Tyr  Asp  Asp  Leu  Glu  Arg  Gln
1                   5                   10                      15

Asn  Trp  Ser  Arg  Pro  Phe  Asn  Gly  Ser  Glu  Gly  Lys  Ala  Asp  Arg  Pro
               20                  25                      30

His  Tyr  Asn  Tyr  Tyr  Ala  Met  Leu  Leu  Thr  Leu  Leu  Ile  Phe  Ile  Ile
          35                  40                      45

Val  Phe  Gly  Asn  Val  Leu  Val  Cys  Met  Ala  Val  Ser  Arg  Glu  Lys  Ala
     50                  55                      60

Leu  Gln  Thr  Thr  Thr  Asn  Tyr  Leu  Ile  Val  Ser  Leu  Ala  Val  Ala  Asp
65                       70                  75                           80

Leu  Leu  Val  Ala  Thr  Leu  Val  Met  Pro  Trp  Val  Val  Tyr  Leu  Glu  Val
               85                  90                       95

Val  Gly  Glu  Trp  Lys  Phe  Ser  Arg  Ile  His  Cys  Asp  Ile  Phe  Val  Thr
               100                 105                      110

Leu  Asp  Val  Met  Met  Cys  Thr  Ala  Ser  Ile  Leu  Asn  Leu  Cys  Ala  Ile
          115                 120                      125

Ser  Ile  Asp  Arg  Tyr  Thr  Ala  Val  Ala  Met  Pro  Met  Leu  Tyr  Asn  Thr
     130                 135                      140

Arg  Tyr  Ser  Ser  Lys  Arg  Arg  Val  Thr  Val  Met  Ile  Ala  Ile  Val  Trp
```

|     | 145 |     |     |     | 150 |     |     |     | 155 |     |     |     | 160 |
| --- | --- | --- | --- | --- | --- | --- | --- | --- | --- | --- | --- | --- | --- |
| Val | Leu | Ser | Phe | Thr | Ile | Ser | Cys | Pro | Leu | Ile | Phe | Gln | Leu | Asn | Asn |
|     |     |     |     | 165 |     |     |     |     | 170 |     |     |     |     | 175 |     |
| Thr | Asp | Gln | Asn | Glu | Cys | Ile | Ile | Ala | Asn | Pro | Ala | Phe | Val | Val | Tyr |
|     |     |     | 180 |     |     |     |     | 185 |     |     |     |     | 190 |     |     |
| Ser | Ser | Ile | Val | Ser | Phe | Tyr | Val | Pro | Phe | Ile | Val | Thr | Ile | Leu | Val |
|     |     | 195 |     |     |     |     | 200 |     |     |     |     | 205 |     |     |     |
| Tyr | Ile | Lys | Ile | Tyr | Ile | Val | Leu | Arg | Lys | Arg | Arg | Lys | Arg | Val | Asn |
|     | 210 |     |     |     |     | 215 |     |     |     |     | 220 |     |     |     |     |
| Thr | Lys | Arg | Ser | Ser | Arg | Ala | Phe | Arg | Ala | Asn | Leu | Lys | Thr | Pro | Leu |
| 225 |     |     |     |     | 230 |     |     |     |     | 235 |     |     |     |     | 240 |
| Lys | Asp | Ala | Ala | Arg | Arg | Ala | Gly | Glu | Leu | Glu | Met | Glu | Met | Leu | Ser |
|     |     |     |     | 245 |     |     |     |     | 250 |     |     |     |     | 255 |     |
| Ser | Thr | Ala | Pro | Pro | Glu | Arg | Thr | Arg | Tyr | Ser | Pro | Ile | Pro | Pro | Ser |
|     |     |     | 260 |     |     |     |     | 265 |     |     |     |     | 270 |     |     |
| His | His | Gln | Leu | Thr | Leu | Pro | Asp | Pro | Ser | His | His | Gly | Leu | His | Ser |
|     |     | 275 |     |     |     |     | 280 |     |     |     |     | 285 |     |     |     |
| Asn | Pro | Asp | Ser | Pro | Ala | Lys | Pro | Glu | Lys | Asn | Gly | His | Ala | Lys | Ile |
|     | 290 |     |     |     |     | 295 |     |     |     |     | 300 |     |     |     |     |
| Val | Asn | Pro | Arg | Ile | Ala | Lys | Phe | Phe | Glu | Ile | Gln | Thr | Met | Pro | Asn |
| 305 |     |     |     |     | 310 |     |     |     |     | 315 |     |     |     |     | 320 |
| Gly | Lys | Thr | Arg | Thr | Ser | Leu | Lys | Thr | Met | Ser | Arg | Arg | Lys | Leu | Ser |
|     |     |     |     | 325 |     |     |     |     | 330 |     |     |     |     | 335 |     |
| Gln | Gln | Lys | Glu | Lys | Lys | Ala | Thr | Gln | Met | Leu | Ala | Ile | Val | Leu | Gly |
|     |     |     | 340 |     |     |     |     | 345 |     |     |     |     | 350 |     |     |
| Val | Phe | Ile | Ile | Cys | Trp | Leu | Pro | Phe | Phe | Ile | Thr | His | Ile | Leu | Asn |
|     |     | 355 |     |     |     |     | 360 |     |     |     |     | 365 |     |     |     |
| Ile | His | Cys | Asp | Cys | Asn | Ile | Pro | Pro | Val | Leu | Tyr | Ser | Ala | Phe | Thr |
|     | 370 |     |     |     |     | 375 |     |     |     |     | 380 |     |     |     |     |
| Trp | Leu | Gly | Tyr | Val | Asn | Ser | Ala | Val | Asn | Pro | Ile | Ile | Tyr | Thr | Thr |
| 385 |     |     |     |     | 390 |     |     |     |     | 395 |     |     |     |     | 400 |
| Phe | Asn | Ile | Glu | Phe | Arg | Lys | Ala | Phe | Met | Lys | Ile | Leu | His | Cys |     |
|     |     |     |     | 405 |     |     |     |     | 410 |     |     |     |     | 415 |     |

(2) INFORMATION FOR SEQ ID NO:11:

(i) SEQUENCE CHARACTERISTICS:
        (A) LENGTH: 466 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (xi) SEQUENCE DESCRIPTION: SEQ ID NO:11:

| Met | Asn | Asn | Ser | Thr | Asn | Ser | Ser | Asn | Asn | Gly | Leu | Ala | Ile | Thr | Ser |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Pro | Tyr | Lys | Thr | Phe | Glu | Val | Val | Phe | Leu | Val | Leu | Val | Ala | Gly | Ser |
|     |     |     | 20  |     |     |     |     | 25  |     |     |     |     | 30  |     |     |
| Ile | Ser | Leu | Val | Thr | Ile | Ile | Gly | Asn | Ile | Leu | Val | Met | Val | Ser | Ile |
|     |     | 35  |     |     |     |     | 40  |     |     |     |     | 45  |     |     |     |
| Lys | Val | Ser | Arg | His | Leu | Gln | Thr | Val | Asn | Asn | Tyr | Phe | Leu | Phe | Ser |

|  |  |  |  | 50 |  |  |  |  | 55 |  |  |  |  | 60 |  |
|---|---|---|---|---|---|---|---|---|---|---|---|---|---|---|---|
| Leu | Ala | Cys | Ala | Asp | Leu | Ile | Ile | Gly | Val | Phe | Ser | Met | Asn | Leu | Tyr |
| 65 | | | | 70 | | | | | 75 | | | | | | 80 |
| Thr | Leu | Tyr | Thr | Val | Ile | Gly | Tyr | Trp | Pro | Leu | Gly | Pro | Val | Val | Cys |
| | | | | 85 | | | | | 90 | | | | | 95 | |
| Asp | Ile | Trp | Leu | Ala | Leu | Asp | Tyr | Val | Val | Ser | Asn | Ala | Ser | Val | Met |
| | | | 100 | | | | | 105 | | | | | 110 | | |
| Asn | Leu | Leu | Ile | Ile | Ser | Phe | Asp | Arg | Tyr | Phe | Cys | Val | Thr | Lys | Pro |
| | | | 115 | | | | 120 | | | | | 125 | | | |
| Leu | Thr | Tyr | Pro | Val | Lys | Arg | Thr | Thr | Lys | Met | Ala | Gln | Met | Met | Ile |
| | 130 | | | | | 135 | | | | | 140 | | | | |
| Ala | Ala | Ala | Trp | Val | Leu | Ser | Phe | Ile | Leu | Trp | Ala | Pro | Ala | Ile | Leu |
| 145 | | | | | 150 | | | | | 155 | | | | | 160 |
| Phe | Trp | Gln | Phe | Ile | Val | Gly | Val | Arg | Thr | Val | Glu | Asp | Gly | Glu | Cys |
| | | | | 165 | | | | | 170 | | | | | 175 | |
| Tyr | Ile | Gln | Phe | Phe | Ser | Asn | Ala | Ala | Val | Thr | Phe | Gly | Thr | Ala | Ile |
| | | | | 180 | | | | | 185 | | | | | 190 | |
| Ala | Ala | Phe | Tyr | Phe | Pro | Val | Ile | Leu | Met | Thr | Val | Leu | Tyr | Trp | His |
| | | | 195 | | | | | 200 | | | | | 205 | | |
| Ile | Ser | Arg | Ala | Ser | Lys | Ser | Arg | Ile | Lys | Lys | Glu | Lys | Lys | Glu | Pro |
| | 210 | | | | | 215 | | | | | 220 | | | | |
| Val | Ala | Asn | Gln | Asp | Pro | Val | Ser | Pro | Ser | Leu | Val | Gln | Gly | Arg | Ile |
| 225 | | | | | 230 | | | | | 235 | | | | | 240 |
| Val | Lys | Pro | Asn | Asn | Asn | Asn | Met | Pro | Gly | Gly | Asp | Gly | Gly | Leu | Glu |
| | | | | 245 | | | | | 250 | | | | | 255 | |
| His | Asn | Lys | Ile | Gln | Asn | Gly | Lys | Ala | Pro | Arg | Asp | Gly | Val | Thr | Glu |
| | | | 260 | | | | | 265 | | | | | 270 | | |
| Thr | Cys | Val | Gln | Gly | Glu | Glu | Lys | Glu | Ser | Ser | Asn | Asp | Ser | Thr | Ser |
| | | | 275 | | | | | 280 | | | | | 285 | | |
| Ser | Ala | Ala | Val | Ala | Ser | Asn | Asn | Arg | Asp | Asp | Glu | Ile | Thr | Gln | Asp |
| | 290 | | | | | 295 | | | | | 300 | | | | |
| Glu | Asn | Thr | Val | Ser | Thr | Ser | Leu | Asp | His | Ser | Arg | Asp | Asp | Asn | Ser |
| 305 | | | | | 310 | | | | | 315 | | | | | 320 |
| Lys | Gln | Thr | Cys | Ile | Lys | Ile | Val | Thr | Lys | Ala | Gln | Lys | Gly | Asp | Val |
| | | | | 325 | | | | | 330 | | | | | 335 | |
| Tyr | Thr | Pro | Thr | Ser | Thr | Thr | Val | Glu | Leu | Val | Gly | Ser | Ser | Gly | Gln |
| | | | 340 | | | | | 345 | | | | | 350 | | |
| Ser | Gln | Asp | Glu | Leu | Gln | Asn | Val | Val | Ala | Arg | Lys | Ile | Val | Lys | Met |
| | | | 355 | | | | | 360 | | | | | 365 | | |
| Pro | Lys | Gln | Pro | Ala | Lys | Lys | Lys | Pro | Pro | Pro | Ser | Arg | Glu | Lys | Lys |
| | 370 | | | | | 375 | | | | | 380 | | | | |
| Val | Thr | Arg | Thr | Ile | Leu | Ala | Phe | Leu | Leu | Ala | Phe | Ile | Ile | Thr | Trp |
| 385 | | | | | 390 | | | | | 395 | | | | | 400 |
| Ala | Pro | Tyr | Asn | Val | Met | Val | Leu | Ile | Asn | Thr | Phe | Cys | Ala | Pro | Cys |
| | | | | 405 | | | | | 410 | | | | | 415 | |
| Ile | Pro | Asn | Thr | Val | Trp | Thr | Ile | Gly | Tyr | Trp | Leu | Cys | Tyr | Ile | Asn |
| | | | 420 | | | | | 425 | | | | | 430 | | |
| Ser | Thr | Ile | Asn | Pro | Ala | Cys | Tyr | Ala | Leu | Cys | Asn | Ala | Thr | Phe | Lys |
| | | 435 | | | | | 440 | | | | | 445 | | | |
| Lys | Thr | Phe | Lys | His | Leu | Leu | Ser | Cys | His | Tyr | Lys | Asn | Ile | Gly | Ala |
| | 450 | | | | | 455 | | | | | 460 | | | | |
| Thr | Arg | | | | | | | | | | | | | | |
| 465 | | | | | | | | | | | | | | | |

( 2 ) INFORMATION FOR SEQ ID NO:12:

( i ) SEQUENCE CHARACTERISTICS:
        ( A ) LENGTH: 788 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( x i ) SEQUENCE DESCRIPTION: SEQ ID NO:12:

```
Met Glu Pro Val Met Ser Leu Ala Leu Ala Ala His Gly Pro Pro Ser
 1               5                  10                  15

Ile Leu Glu Pro Leu Phe Arg Thr Val Thr Ser Thr Thr Thr Thr Thr
                20                  25                  30

Thr Thr Thr Thr Thr Ser Thr Thr Thr Thr Thr Ala Ser Pro Ala Gly
            35                  40                  45

Tyr Ser Pro Gly Tyr Pro Gly Thr Thr Leu Leu Thr Ala Leu Phe Glu
        50                  55                  60

Asn Leu Thr Ser Thr Ala Ala Ser Gly Leu Tyr Asp Pro Tyr Ser Gly
65                  70                  75                  80

Met Tyr Gly Asn Gln Thr Asn Gly Thr Ile Gln Phe Glu Thr Lys Gly
                85                  90                  95

Pro Arg Tyr Ser Leu Ala Ser Met Val Val Met Gly Phe Val Ala Ala
               100                 105                 110

Ile Leu Ser Thr Val Thr Val Ala Gly Asn Val Met Val Met Ile Ser
               115                 120                 125

Phe Lys Ile Asp Lys Gln Leu Gln Thr Ile Ser Asn Tyr Phe Leu Phe
    130                 135                 140

Ser Leu Ala Ile Ala Asp Phe Ala Ile Gly Ala Ile Ser Met Pro Leu
145                 150                 155                 160

Phe Ala Val Thr Thr Ile Leu Gly Tyr Trp Pro Leu Gly Pro Ile Val
               165                 170                 175

Cys Asp Thr Trp Leu Ala Leu Asp Tyr Leu Ala Ser Asn Ala Ser Val
               180                 185                 190

Leu Asn Leu Leu Ile Ile Ser Phe Asp Arg Tyr Phe Ser Val Thr Arg
               195                 200                 205

Pro Leu Thr Tyr Arg Ala Lys Arg Thr Thr Asn Arg Ala Ala Val Met
    210                 215                 220

Ile Gly Ala Ala Trp Gly Ile Ser Leu Leu Leu Trp Pro Pro Trp Ile
225                 230                 235                 240

Tyr Ser Trp Pro Tyr Ile Glu Gly Lys Arg Thr Val Pro Lys Asp Glu
               245                 250                 255

Cys Tyr Ile Gln Phe Ile Glu Thr Asn Gln Tyr Ile Thr Phe Gly Thr
               260                 265                 270

Ala Leu Ala Ala Phe Tyr Phe Pro Val Thr Ile Met Cys Phe Leu Tyr
    275                 280                 285

Trp Arg Ile Trp Arg Glu Thr Lys Lys Arg Gln Lys Asp Leu Pro Asn
    290                 295                 300

Leu Gln Ala Gly Lys Lys Asp Ser Ser Lys Arg Ser Asn Ser Ser Asp
305                 310                 315                 320
```

```
Glu  Asn  Thr  Val  Val  Asn  His  Ala  Ser  Gly  Gly  Leu  Leu  Ala  Phe  Ala
               325                 330                           335

Gln  Val  Gly  Gly  Asn  Asp  His  Asp  Thr  Trp  Arg  Arg  Pro  Arg  Ser  Glu
               340                 345                           350

Ser  Ser  Ala  Asp  Ala  Glu  Ser  Val  Tyr  Met  Thr  Asn  Met  Val  Ile  Asp
               355                 360                           365

Ser  Gly  Tyr  His  Gly  Met  His  Ser  Arg  Lys  Ser  Ser  Ile  Lys  Ser  Thr
     370                      375                 380

Asn  Thr  Ile  Lys  Lys  Ser  Tyr  Thr  Cys  Phe  Gly  Ser  Ile  Lys  Glu  Trp
385                      390                 395                           400

Cys  Ile  Ala  Trp  Trp  His  Ser  Gly  Arg  Glu  Asp  Ser  Asp  Asp  Phe  Ala
               405                 410                           415

Tyr  Glu  Gln  Glu  Glu  Pro  Ser  Asp  Leu  Gly  Cys  Thr  Ser  Met  Asn  Val
               420                 425                           430

Met  Arg  Asp  Asn  Tyr  Ser  Met  Gly  Gly  Ser  Val  Ser  Ala  Val  Arg  Pro
          435                      440                 445

Pro  Ser  Ile  Leu  Leu  Ser  Asp  Val  Ser  Pro  Thr  Pro  Leu  Pro  Arg  Pro
     450                      455                 460

Pro  Leu  Ala  Ser  Ile  Ser  Gln  Leu  Gln  Glu  Met  Ser  Ala  Val  Thr  Ala
465                      470                 475                           480

Ser  Thr  Thr  Ala  Asn  Val  Asn  Thr  Ala  Gly  Asn  Gly  Asn  Gly  Ala  Ile
               485                 490                           495

Asn  Asn  Asn  Asn  Asn  Ala  Ser  His  Asn  Gly  Asn  Gly  Ala  Val  Asn  Gly
               500                 505                           510

Asn  Gly  Ala  Gly  Asn  Gly  Ala  Gly  Ile  Gly  Leu  Gly  Thr  Thr  Gly  Asn
          515                      520                 525

Ala  Thr  His  Arg  Asp  Ser  Arg  Thr  Leu  Pro  Val  Ile  Asn  Arg  Ile  Asn
     530                      535                 540

Ser  Arg  Ser  Val  Ser  Gln  Asp  Ser  Val  Tyr  Thr  Ile  Leu  Ile  Arg  Leu
545                      550                 555                           560

Pro  Ser  Asp  Gly  Ala  Ser  Ser  Asn  Ala  Ala  Asn  Gly  Gly  Gly  Gly  Gly
               565                 570                           575

Pro  Gly  Ala  Gly  Ala  Ala  Ala  Ser  Ala  Ser  Leu  Ser  Met  Gln  Gly  Asp
               580                 585                           590

Cys  Ala  Pro  Ser  Ile  Lys  Met  Ile  His  Glu  Asp  Gln  Pro  Thr  Thr  Thr
          595                      600                 605

Ala  Ala  Ala  Ala  Pro  Leu  Ala  Ser  Ala  Ala  Ala  Thr  Arg  Arg  Pro  Leu
     610                      615                 620

Pro  Ser  Arg  Asp  Ser  Glu  Phe  Ser  Leu  Pro  Leu  Gly  Arg  Arg  Met  Ser
625                      630                 635                           640

His  Ala  Gln  His  Asp  Ala  Arg  Leu  Leu  Asn  Ala  Lys  Val  Ile  Pro  Lys
               645                 650                           655

Gln  Leu  Gln  Lys  Ala  Gly  Gly  Ala  Ala  Gly  Gly  Gly  Val  Gly  Gly
               660                 665                           670

Ala  His  Ala  Leu  Met  Asn  Ala  Arg  Asn  Ala  Ala  Lys  Lys  Lys  Lys
          675                      680                 685

Ser  Gln  Glu  Lys  Arg  Gln  Glu  Ser  Lys  Ala  Ala  Lys  Thr  Leu  Ser  Ala
     690                      695                 700

Ile  Leu  Leu  Ser  Phe  Ile  Ile  Thr  Trp  Thr  Pro  Tyr  Asn  Ile  Leu  Val
705                      710                 715                           720

Leu  Ile  Lys  Pro  Leu  Thr  Thr  Cys  Ser  Asp  Cys  Ile  Pro  Thr  Glu  Leu
               725                 730                           735
```

```
Trp  Asp  Phe  Phe  Tyr  Ala  Leu  Cys  Tyr  Ile  Asn  Ser  Thr  Ile  Asn  Pro
               740                 745                      750

Met  Cys  Tyr  Ala  Leu  Cys  Asn  Ala  Thr  Phe  Arg  Arg  Thr  Tyr  Val  Arg
          755                 760                      765

Ile  Leu  Thr  Cys  Lys  Trp  His  Thr  Arg  Asn  Arg  Glu  Gly  Met  Val  Arg
          770                 775                      780

Gln  Val  Tyr  Asn
785
```

( 2 ) INFORMATION FOR SEQ ID NO:13:

( i ) SEQUENCE CHARACTERISTICS:
    ( A ) LENGTH: 460 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( x i ) SEQUENCE DESCRIPTION: SEQ ID NO:13:

```
Met  Val  Asn  Leu  Gly  Asn  Ala  Val  Arg  Ser  Leu  Leu  Met  His  Leu  Ile
1              5                   10                      15

Gly  Leu  Leu  Val  Trp  Gln  Phe  Asp  Ile  Ser  Ile  Ser  Pro  Val  Ala  Ala
               20                 25                      30

Ile  Val  Thr  Asp  Thr  Phe  Asn  Ser  Ser  Asp  Gly  Gly  Arg  Leu  Phe  Gln
          35                      40                 45

Phe  Pro  Asp  Gly  Val  Gln  Asn  Trp  Pro  Ala  Leu  Ser  Ile  Val  Val  Ile
     50                      55                      60

Ile  Ile  Met  Thr  Ile  Gly  Gly  Asn  Ile  Leu  Val  Ile  Met  Ala  Val  Ser
65                  70                      75                           80

Met  Glu  Lys  Lys  Leu  His  Asn  Ala  Thr  Asn  Tyr  Phe  Leu  Met  Ser  Leu
               85                      90                      95

Ala  Ile  Ala  Asp  Met  Leu  Val  Gly  Leu  Leu  Val  Met  Pro  Leu  Ser  Leu
          100                      105                     110

Leu  Ala  Ile  Leu  Tyr  Asp  Tyr  Val  Trp  Pro  Leu  Pro  Arg  Tyr  Leu  Cys
          115                      120                     125

Pro  Val  Trp  Ile  Ser  Leu  Asp  Val  Leu  Phe  Ser  Thr  Ala  Ser  Ile  Met
     130                      135                     140

His  Leu  Cys  Ala  Ile  Ser  Leu  Asp  Arg  Tyr  Val  Ala  Ile  Arg  Asn  Pro
145                      150                     155                     160

Ile  Glu  His  Ser  Arg  Phe  Asn  Ser  Arg  Thr  Lys  Ala  Ile  Met  Lys  Ile
                    165                     170                     175

Ala  Ile  Val  Trp  Ala  Ile  Ser  Ile  Gly  Val  Ser  Val  Pro  Ile  Pro  Val
               180                     185                     190

Ile  Gly  Leu  Arg  Asp  Glu  Ser  Lys  Val  Phe  Val  Asn  Asn  Thr  Thr  Cys
          195                     200                     205

Val  Leu  Asn  Asp  Pro  Asn  Phe  Val  Leu  Ile  Gly  Ser  Phe  Val  Ala  Phe
     210                     215                     220

Phe  Ile  Pro  Leu  Thr  Ile  Met  Val  Ile  Thr  Tyr  Phe  Leu  Thr  Ile  Tyr
225                     230                     235                     240

Val  Leu  Arg  Arg  Gln  Thr  Leu  Met  Leu  Leu  Arg  Gly  His  Thr  Glu  Glu
                    245                     250                     255
```

```
Glu  Leu  Ala  Asn  Met  Ser  Leu  Asn  Phe  Leu  Asn  Cys  Cys  Cys  Lys  Lys
               260                 265                      270

Asn  Gly  Gly  Glu  Glu  Glu  Asn  Ala  Pro  Asn  Pro  Asn  Pro  Asp  Gln  Lys
          275                      280                      285

Pro  Arg  Arg  Lys  Lys  Lys  Glu  Lys  Arg  Pro  Arg  Gly  Thr  Met  Gln  Ala
     290                      295                      300

Ile  Asn  Asn  Glu  Lys  Lys  Ala  Ser  Lys  Val  Leu  Gly  Ile  Val  Phe  Phe
305                           310                 315                      320

Val  Phe  Leu  Ile  Met  Trp  Cys  Pro  Phe  Phe  Ile  Thr  Asn  Ile  Leu  Ser
                    325                      330                      335

Val  Leu  Cys  Gly  Lys  Ala  Cys  Asn  Gln  Lys  Leu  Met  Glu  Lys  Leu  Leu
               340                      345                      350

Asn  Val  Phe  Val  Trp  Ile  Gly  Tyr  Val  Cys  Ser  Gln  Ile  Asn  Pro  Ile
          355                      360                      365

Val  Tyr  Thr  Leu  Phe  Asn  Lys  Ile  Tyr  Arg  Arg  Ala  Phe  Ser  Lys  Tyr
     370                      375                      380

Leu  Arg  Cys  Asp  Tyr  Lys  Pro  Asp  Lys  Lys  Pro  Pro  Val  Arg  Gln  Ile
385                      390                      395                      400

Pro  Arg  Val  Ala  Ala  Thr  Ala  Leu  Ser  Gly  Arg  Glu  Ile  Asn  Val  Asn
               405                      410                      415

Ile  Tyr  Arg  His  Thr  Asn  Glu  Arg  Val  Ala  Arg  Lys  Ala  Asn  Asp  Pro
               420                      425                      430

Glu  Pro  Gly  Ile  Glu  Met  Gln  Val  Glu  Asn  Leu  Glu  Leu  Pro  Val  Asn
          435                      440                      445

Pro  Glu  Asn  Val  Val  Ser  Glu  Arg  Ile  Ser  Ser  Val
     450                      455                      460
```

( 2 ) INFORMATION FOR SEQ ID NO:14:

( i ) SEQUENCE CHARACTERISTICS:
        ( A ) LENGTH: 63 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:14:

```
Val  Gly  Asn  Val  Leu  Val  Ala  Leu  Asn  Ile  Leu  Ala  Ala  Asp  Val  Gly
1                   5                   10                           15

Met  Trp  Gly  Cys  Trp  Asp  Leu  Ala  Ser  Ile  Leu  Ile  Ser  Asp  Arg  Tyr
               20                  25                       30

Pro  Thr  Ile  Ile  Asn  Ser  Ser  Phe  Tyr  Pro  Ile  Tyr  Glu  Lys  Leu  Ile
          35                  40                       45

Phe  Leu  Trp  Pro  Phe  Tyr  Ser  Asn  Pro  Tyr  Phe  Arg  Ala  Phe  Leu
     50                  55                       60
```

( 2 ) INFORMATION FOR SEQ ID NO:15:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:15:

CTAGATGCCA TCGGCAGATC AAATCAAATC   30

(2) INFORMATION FOR SEQ ID NO:16:

(i) SEQUENCE CHARACTERISTICS:
  (A) LENGTH: 18 base pairs
  (B) TYPE: nucleic acid
  (C) STRANDEDNESS: single
  (D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:16:

TACGGTAGCC GTCTAGTT   18